United States Patent [19]
Heintz et al.

[11] Patent Number: 5,928,871
[45] Date of Patent: Jul. 27, 1999

[54] CDNA COLLECTIONS ENCODING PROTEINS REGULATED DURING PROGRAMMED CELL DEATH, AND METHOD OF USE THEREOF

[75] Inventors: Nathaniel Heintz, Pelham Manor, N.Y.; John Gubbay, London, United Kingdom; Michael K. Skinner, Pullman, Wash.

[73] Assignee: The Rockefeller University, New York, N.Y.

[21] Appl. No.: 08/925,171

[22] Filed: Sep. 8, 1997

Related U.S. Application Data

[63] Continuation-in-part of application No. 08/751,782, Nov. 18, 1996, Pat. No. 5,821,352.
[51] Int. Cl.$^6$ .............................. C12Q 1/68; C12N 15/12; C07H 21/00
[52] U.S. Cl. .......................... 435/6; 536/23.5; 536/24.31
[58] Field of Search ................. 435/6; 536/23.1, 536/23.2, 23.5, 24.3, 24.31

[56] References Cited

U.S. PATENT DOCUMENTS 5,525,471 6/1996 Zeng ............................................ 435/6

OTHER PUBLICATIONS

Briehl et al. (1991) Mol. Endocrinol. 5:1381–8.
Leger et al., Biochem. Biophy. Res. Comm. 147:196–203 (1987).
Wang et al. (1993) J. Biol. Chem. 268:16270–8.
Shaw et al. (1988) Cloning and sequencing of cDNA encoding a rat salivary cysteine proteinase inhibitor inducible by beta–adrenergic agonists. J. Biol. Chem. 263:18133–18137, Dec. 1988.
Wodnar–Filipowicz et al. (1984) Cloning and sequence analysis of cDNA for rat spleen thymosin beta 4. Proc. Natl. Acad. Sci. USA 81:2295–2297, Apr. 1984.

*Primary Examiner*—George C. Elliott
*Assistant Examiner*—Robert Schwartzman
*Attorney, Agent, or Firm*—Klauber & Jackson

[57] ABSTRACT

The present invention identifies cDNA collections enriched in genes regulated in prostate homeostasis, prostate regression, and in genes regulated in programmed cell death. These novel cDNA collections provide cDNAs that encode proteins that are either unique to general programmed cell death or unique to prostate regression. These transcripts can be used as markers to screen, monitor and/or to diagnose diseased conditions including prostate cancer. In addition, these cDNA collections can be used in methods of designing novel therapeutic agents useful for treating prostate cancer. Methods of making these collections through subtraction hybridization are described.

41 Claims, 8 Drawing Sheets

-8 cDNA

SGP-2

GAPDH probe: +10cDNA            SGP-2

10.19

10.17

10.3

10.8

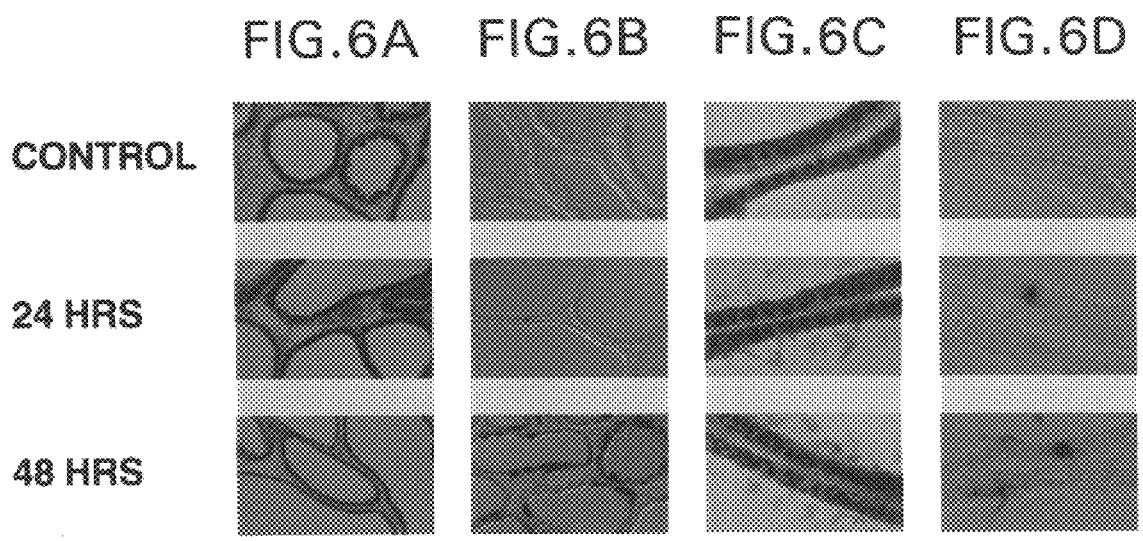

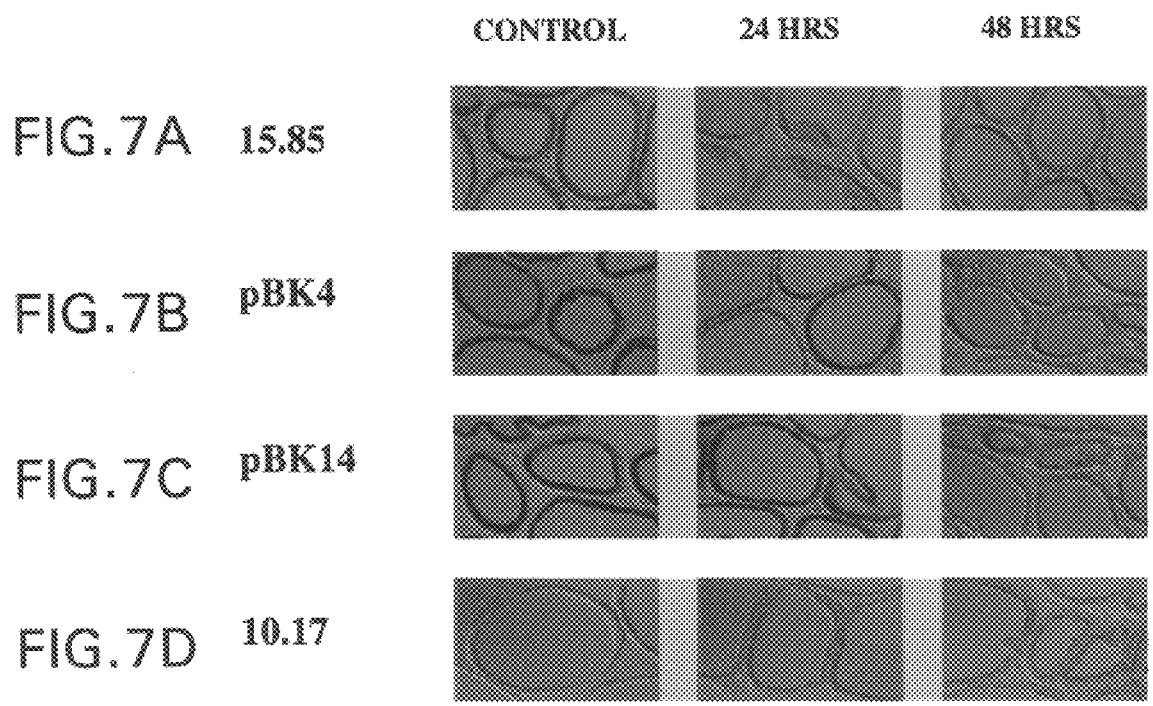

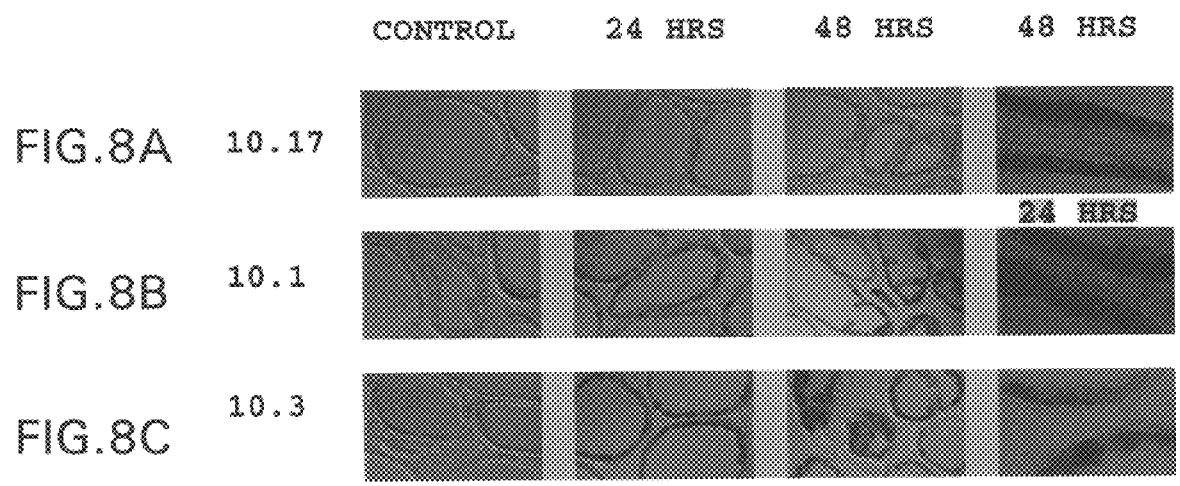

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 458 base pairs
      (B) TYPE: nucleic acid
      (C) STRANDEDNESS: double (D) TOPOLOGY: linear (ii) MOLECULE TYPE: cDNA (iii) HYPOTHETICAL: NO (vii) IMMEDIATE SOURCE:
              (B) CLONE: 10.4

(xi) SEQUENCE DESCRIPTION: SEQ ID NO:1:

CTGAAACGGG CCCNCCCTCG AGGTCGACGG CCTCGATAAG CTTGATATCG AATTCGGACT      60

AGTGGGCAGG CTCCGCAGGA CAGCTAGCAG CGCTTCCTCC TGGGATTCAG TCATTTAAAG     120

ATTGAGACCA AGATTGAAAG CATGGCTGAC CTCAAGCAGC TCATGGACAA CGAGGTGTTG     180

ATGGCCTCTA CCTCCTATTT AACGATCATT CTTGCCAAGA TGATGTTCCT GAGCTCCGCG     240

ACTGCATTCC AGAGGCTAAC CAACAAGGTT TTTGNCAACC CGGAAGACTG TGCTGGCTTC     300

GGCAAGGGGG AGAATGCCAA GAAGTTCCTT CGGACTGACG AGAGGGTGGG AACGCGTCTC     360

GAAAGAGCCC ACCTGAATGA ACTTGAAANC ATCNGNNCCC CTTTCTTCGG TATCGGGNCT     420

CCTGTTAGTC CCNAATTTCC TGCAGNCCGG GGGGATCC                            458

(2) INFORMATION FOR SEQ ID NO:2:

(i) SEQUENCE CHARACTERISTICS:
              (A) LENGTH: 178 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (vii) IMMEDIATE SOURCE:
              (B) CLONE: 10.2

(xi) SEQUENCE DESCRIPTION: SEQ ID NO:2:

GGACTAAGGA AACATGTGCG CCTAGACCCA GATTCTAAAG AATTTTGGGA TTTTAGTTTT      60

AATGAACAAA TAGAATACGA CCTCCCAGCC ATCATTTATT TCATTCTGAA TGAAACAAGA     120

CAAACACAAA TTTACTATAT TGGCCATTCC CAGGGCGTCT ATCTGCGTAT CAGCATTT      178

(2) INFORMATION FOR SEQ ID NO:3:

(i) SEQUENCE CHARACTERISTICS:
              (A) LENGTH: 136 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (vii) IMMEDIATE SOURCE:
              (B) CLONE: 10.5

(xi) SEQUENCE DESCRIPTION: SEQ ID NO:3:

AGAAGATCAT GGCCTACCTG CTCCATGCTC AACTATTTCT ACTGACTACC TTTATATTAG      60

TTTTGAACAT GAGACTTTGT CCTGTTCTAG GTCACTTTCT GGGTGGCATA GAGAAGTCTA     120

GCATGGAGGA GGAAGG                                                    136

(2) INFORMATION FOR SEQ ID NO:4:

(i) SEQUENCE CHARACTERISTICS:
              (A) LENGTH: 132 base pairs (B) TYPE: nucleic acid
    (C) STRANDEDNESS: double
    (D) TOPOLOGY: linear (ii) MOLECULE TYPE: cDNA (iii) HYPOTHETICAL: NO (vii) IMMEDIATE SOURCE:
    (B) CLONE: 10.8

(xi) SEQUENCE DESCRIPTION: SEQ ID NO:4:

```
ACGAGAACAT GCCTCTCGCA AAGGATCTCC TACANCCTTC TCCAGANGNG GAGAAGAGGA    60

AACACAAGAA AACGCGCCTG GTGCAGAGCC CCAATTCCTA CTTNTTGGAT GTGAAATGTC   120

CAGGATGCTA TA                                                      132
```

(2) INFORMATION FOR SEQ ID NO:5:

(i) SEQUENCE CHARACTERISTICS:
    (A) LENGTH: 685 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (vii) IMMEDIATE SOURCE:
    (B) CLONE: 10.12

(xi) SEQUENCE DESCRIPTION: SEQ ID NO:5:

```
CCCCCCCCN NNTTTTNAAN CNCTTAAACC GGGCCCCCCT CGANGTCGAC GGTCTCGATA    60

AGCTTGATAT CGACTTCGGA CTAGGGTGAG GGACCTCTGC TGCGCTGGCT CAAGGTGAAC   120

TTCAGCGAGG CCTTTATTGC CTGGATCCAC ATAAAGGCCC TGAGAGTGTT TGTGGAGTCT   180

GTGCTCAGGT ATGGACTTCC AGTGAACTTC CAGGCTGTGC TCCTGNAGCC CCATAAAAAG   240

TCTGCCACCA AACGCCTGAG AGAGGTGCTC AATTCGGTCT TCCGGCACCT GGATGAAGTN   300

GCTGCAGCAA GCATACTGGA TGCATCCGTG GAGATCCCTG GCCTGCAGCT CAGCAAACCA   360

GGACTATTTC CCCTACGTGT TAGTCCGAAT TCCCTGNAGN CCGGGGGGAT CCACTAGTTC   420

TAGAGCGGNC CGCCACGGGG TGGGAGCTCC AATTCGCCCN ATTNGTGAGT CCGNNTTACA   480

AATCANTGGN CGNTCGGTTT NNCAAGNTNC GNTGATTGGT AAAACCCNNG NGTTACCCAA   540

NTNAATCGCC TTGNAGGAAA NTCCCCCCNC GCAAGTNGGN TATAGGAAAG NGGCCCCACC   600

CTNCGCCTCC CANAGTNCGA GCCTNNTTNG ATGGACNGCC CNTGCGNCAT TACNNGGNGG   660

GGGGNTTTGN TAANTNACNT TAATN                                        685
```

(2) INFORMATION FOR SEQ ID NO:6:

(i) SEQUENCE CHARACTERISTICS:
    (A) LENGTH: 174 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (vii) IMMEDIATE SOURCE:
    (B) CLONE: 10.13

(xi) SEQUENCE DESCRIPTION: SEQ ID NO:6:

```
GAAGTCTTTA CACTGAAGGA GGCTCTGAAG GTGCAGCAGT CCACTCCAGC CAGCTCCAAG    60
```

```
GAGCAGGAGG AGNNNCTGCG TGGTCAGGTG ACAGCCTTGC AACANAGATA CAGGAGGANN        120

NCAGGAACAC TCGACTGTGG TGGCTTTATA CCGNACCCAT CTCCCTGTTA GTCC              174

(2) INFORMATION FOR SEQ ID NO:7:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: 10.15

(xi) SEQUENCE DESCRIPTION: SEQ ID NO:7:

TGAAAATGTC AGATATTAGA TACAATGCAT TTGGATCATA GTCTTCCCCT CCAACTCTCC        60

TATTTCTGTC TCCTATGCCC TCCCAGTTGC CCATCTTCCT CAGAACTGCA TCTCTGAAGA       120

AAACTGACCC TCCTCCNNNT GGCACCACTG CCATTAGCTC TGCAGTGAGG GGTGGGAACT       180

CATGAGTAGT CC                                                           192

(2) INFORMATION FOR SEQ ID NO:8:

(i) SEQUENCE CHARACTERISTICS:
        (A) LENGTH: 208 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: 10.16

(xi) SEQUENCE DESCRIPTION: SEQ ID NO:8:

GGACTAACCA AGCAATGCAC TCATTCCTGC GATAATGGTG AGGGCGGTGA TGATGATGAC        60

GGAGACAGCT TTTGTCTTGA CTGCAGTTTG GGGCTCAGCA ATGATCGGCA AGCGCTCTGG       120

TTTCTGGTTG TCAGTGGTGA GACCAGTAAC ATCCAGGGNG AAGTTTTTGA AATTTTTCTG       180

GAATCCACTC AGCTTCCACC AGTAGTCC                                          208

(2) INFORMATION FOR SEQ ID NO:9:

(i) SEQUENCE CHARACTERISTICS:
        (A) LENGTH: 259 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: 10.20

(xi) SEQUENCE DESCRIPTION: SEQ ID NO:9:

GGNCTAGTGC ACAGGAAATC CATCTTCAGA TGNACAGGAA AACACATCTT CAGGTGANCG        60

GACAGAAANC CCACATTCTG TGNTCATGTG TANCTGTCAT CCAGTGAAGA AGTANGTGNA       120

NAAGTCACAG TGTTCTGNGT GCCAAGGGCA CGTTATAGTG TTNTTCTTTT TCATCTGGGA       180
```

```
ACGAGNACCC NCCCGGNCTC TGAGTNTGAC CGTTCTATCC ACCTTANCTC CATAGCCGAA      240

TCCNGNAGCC CCGGGATCC                                                  259
```

(2) INFORMATION FOR SEQ ID NO:10:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: 10.23

(xi) SEQUENCE DESCRIPTION: SEQ ID NO:10:

```
GCGATCCCCT TCAACGNGGT GGNCCCGCTA TAGAACTAGT GNATCCCCCG GNCTGNAGGA       60

ATCCGGACTA ACGGACCCTG CGGCCAGTGG TCTTGGTGTG CTGACCCCGG ACACGAAGGC      120

CCCAAAAGTG GCGCAGCCCT CTATGGGCTC GGATTTTCTT CAGNCGCTCC AGGTCCTCAC      180

GNAGGTTGTT GTCTAGACCG CTGGNCAGAA CCTGGCTATT TTTCTTNTCC TTCACGTCCT      240

TCTGTCTGTT CAAGAACCAG TCAGGGATCT TGTATTGTNG CGGGTTCTGN ATNATGGTGA      300

TCACACGNTC CACCTCGTCC TCCCGGANTA GTCCGTATTC GGTNTCATGC TTTATCGATN      360

CCTCCGNCCT CNAGGGGGGG GCNGGGCACC ANATTTCAGT TCCCCNTTCA GTNCATGNNT      420

AAAATTTCGG NNNTTGGTGN NCATCAACNG ACNAAANCTG NNTTCCCNCC GTGAACTTNT      480

AATTCCCCTC ACATACTCTN CAAAANTAAT TTAT                                 514
```

(2) INFORMATION FOR SEQ ID NO:11:

(i) SEQUENCE CHARACTERISTICS:
        (A) LENGTH: 182 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (B) CLONE: 10.27

(xi) SEQUENCE DESCRIPTION: SEQ ID NO:11:

```
ACAAACCCGA TATGGCTGAG ATCGAGAAAT TCGATAAGTC GAAGTTGAAG AAGACAGAAA       60

CACAAGAGAA AAATCCTCTG CCTTCAAAAG AAACAATTGA ACAAGAGAAG CAAGCTGGCG      120

AATCGTAATG AGGCGAGCGG CAATATGCAC TGTTAGTCGA ATTCGCATAT GGGAATCAGA      180

AT                                                                    182
```

(2) INFORMATION FOR SEQ ID NO:12:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
    (B) CLONE: 10.28

(xi) SEQUENCE DESCRIPTION: SEQ ID NO:12:

```
ATCAGCTGAA ACAGACTCTC TGACAGTGAC TTTGAAGTCT CAGCTGCATC CCTCTGGAGA      60
GCGACCNNCC TCACTGCTTC TGTTCCCTTA TCTGGAGGAT GGGGACTGAG TGAGGGCCAT     120
CTGCTGTGAG ATGGCACAGA AGATG                                          145
```

(2) INFORMATION FOR SEQ ID NO:13:

(i) SEQUENCE CHARACTERISTICS:
       (A) LENGTH: 230 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vii) IMMEDIATE SOURCE:
       (B) CLONE: 10.29

(xi) SEQUENCE DESCRIPTION: SEQ ID NO:13:

```
GGACTACTGG CTAGGTTACG GTCTAAAATT ATTAGCGTTG CATTGTCTCG TATGCAAACT      60
AAGTCTCTTC TGCGCACTTT CTCATTGGAG GGCTAGGTGT GGTGGCTCCA CCCACCAACT     120
GGGAAGCGCT CTGAATGCTG TGTCTGGTCG GTCTGTGCGA ATGAATTTTC TTGTATGCCG     180
GNTGATTATG TTAACGGAGG CGTTTAATGT TGCGTGCCAG GCTGCAAGGG                230
```

(2) INFORMATION FOR SEQ ID NO:14:

(i) SEQUENCE CHARACTERISTICS:
       (A) LENGTH: 195 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vii) IMMEDIATE SOURCE:
       (B) CLONE: 10.30

(xi) SEQUENCE DESCRIPTION: SEQ ID NO:14:

```
GGACTAGAAA CAAGTGCCTT CAGTAACTTT TGTCCCAGGG TTACAAATTT GAAAATTTGA      60
TTATACTAAA CCAATACAAG CTTATATAAG TGTTTCAGTT ATTTTCTAAT TTCAAGCACA     120
AACAAGGAAA CAAAAGTTAA ATGACACACT TAGTTACTCT TGTAACCAGC TCTGGTTAGT     180
CCGAATTCGG ACTAG                                                     195
```

(2) INFORMATION FOR SEQ ID NO:15:

(i) SEQUENCE CHARACTERISTICS:
       (A) LENGTH: 252 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (vii) IMMEDIATE SOURCE:
       (B) CLONE: 15.8

(xi) SEQUENCE DESCRIPTION: SEQ ID NO:15:

-continued

```
AAAGAATTCG GCACGAGAAG AATTTTGGTG GATATTTGGT AAACATATTG ATAAAGGAAA        60

AGTAAGAGTG TGAGAAGAGA GATGAGATTT GTGGGGTAAT AGATGATGCA GAGAATAGAA       120

ACGAAGGATG AGAATGAAGG CATAAAGCAG GGACTAGGAG AAGGATTGTG TTGAAGGGAT       180

TGTTAGCCAT GTAGGAGGGA GGAATGTGTG TAATAGGAAT GTGTGTATAG GAAGTGGATG       240

AGTGTAAGTG TG                                                          252
```

CDNA COLLECTIONS ENCODING PROTEINS REGULATED DURING PROGRAMMED CELL DEATH, AND METHOD OF USE THEREOF

CROSS-REFERENCE TO RELATED APPLICATIONS

The present Application is a Continuation-In-Part of U.S. Ser. No. 08/751,782, filed Nov. 18, 1996, U.S. Pat. No. 5,821,352, the disclosure of which is hereby incorporated by reference in its entirety. Applicants claim the benefits of this Application under 35 U.S.C. § 120.

FIELD OF THE INVENTION

The invention relates generally to enriched prostate regression cDNA libraries and methods of using these libraries to identify nucleic acids encoding proteins that are either induced or suppressed during prostate regression. The invention includes the enriched prostate regression cDNA libraries and methods of use and preparation thereof.

BACKGROUND OF THE INVENTION

Proper regulation of the growth and death of individual cells is fundamental for the development and normal function of complex organisms. An understanding of cell growth control is emerging from genetic, molecular and biochemical studies in many organisms that have lead to a detailed mechanistic description of the cell cycle and its regulation. The realization that, similar to cell growth, cell death is an orderly process that is critical for organogenesis, and that abnormal regulation of cell death can be a critical initiating event in human disease, has stimulated a great deal of interest in discovering its mechanistic basis. Genetic studies of the stereotyped death of individual cells during development of C. elegans have led to identification of several genes that are regulators of programmed cell death, and have provided a gross outline for the cell death pathway. Convincing evidence that some of these molecules are fundamental participants in the cell death pathway in all metazoans has emerged from parallel studies of mammalian genes first identified in the context of oncogenesis and later shown to allow abnormal cell expansion due to failures in programmed cell death. For example, the C. elegans ced 9 gene and the mammalian bcl-2 gene are demonstrated functional homologues that can prevent programmed death in both insect and mammalian cells. The mammalian ICE like proteases and C. elegans ced 3 genes are also functionally homologous, although in this case their role is to induce apoptotic death. While definition of the specific mechanisms through which these molecules act is an area of intense investigation, an appreciation that the program mediating cell death may be as complex as that regulating cell growth is also emerging.

In the absence of testosterone, programmed cell death is triggered in the prostate and the prostate dies. Therefore, a castrated mammal may be used as an experimental animal model for programmed cell death. During this process, certain detrimental genes will presumably be turned on, and certain genes necessary for a normal, healthy prostate will presumably be turned off. Such an experimental animal model may be used to study mechanisms related to programmed cell death, most notably cancer.

Recent studies indicate that all human males will eventually develop prostate cancer, if they live long enough. For example, 50% of all men over 50 and essentially all men over 70 suffer from some form of prostate hyperplasia. Annually, 250,000 new cases of prostate cancer are diagnosed, and despite the $4 billion dollars spent to treat this ailment, 40,000 men die of prostate cancer each year. As the United States population continues to age, due to the aging of the post-World War II baby boomers, these numbers can only be expected to rise.

One particular aspect of prostate cancer is that it oftentimes strikes relatively late in life and then progresses slowly. Thus, for many older men, the best treatment would be to simply monitor the progression of the cancer rather than aggressively attack it, since under such circumstances it is far more likely that the patient will succumb to other causes of death, long before the prostate cancer becomes life-threatening. Unfortunately, there presently exists a definite lack of a means for accurately monitoring and more importantly, accurately predicting the progression of prostate cancer. Current technology relies on monitoring the protein PSA, which can result in a high percentage of false positives, and cannot be used as a predictor of the future progression of the disease. Therefore, there is a need to identify means of obtaining other factors that could be diagnostic of prostate cancer. Furthermore, there is a need to identify means that can be used to predict the future progression of prostate hyperplasia. Finally, there is a need to identify means that can be used to identify stages of prostate regression.

The citation of any reference herein should not be construed as an admission that such reference is available as "Prior Art" to the instant application.

SUMMARY OF THE INVENTION

The present invention includes the identification and isolation of mRNAs that are regulated during programmed cell death. These mRNAs are compiled as their cognate cDNAs in cDNA collections that are significantly enriched for such mRNAs. The cDNA collections include cDNAs that either encode proteins that are generally regulated during programmed cell death, or are uniquely regulated during prostate regression. Such cDNAs are valuable as markers to monitor and/or to diagnose patients suspected of having tissues undergoing programmed cell death including those of whom have been medically induced to undergo such programmed cell death, e.g., as treatment for a cancerous tumor.

The present invention includes methods of preparing a prostate regression cDNA collection enriched in cDNAs for genes that are regulated at a specified time-period during about the first 48 hours following the initiation of prostate regression, including genes that are regulated throughout the entire 48 time-period. One such method comprises initiating prostate regression in a male animal (i.e., an animal having a prostate) and collecting mRNAs from the prostate within about the first 48 hours following the initiation of prostate regression. Cognate cDNAs are prepared from the collected mRNAs and subtraction hybridization is performed on the cognate cDNAs. The prostate regression cDNA collection prepared is enriched in cDNAs for genes that are regulated during about the first 48 hours following the initiation of prostate regression. For example, in one such embodiment a cDNA collection can be prepared to be enriched in cDNAs for genes that are regulated between the time-period between 12 and 24 hours following the initiation of prostate regression.

In one such embodiment mRNAs are collected between 0 and 52 hours following the initiation of prostate regression.

In another embodiment the mRNAs are collected between 3 hours and 45 hours following the initiation of prostate regression. In another embodiment the mRNAs are collected between 6 hours and 36 hours following the initiation of prostate regression. In yet another embodiment the mRNAs are collected between 9 hours and 27 hours following the initiation of prostate regression. In still another embodiment the mRNAs are collected between 12 hours and 18 hours following the initiation of prostate regression.

In a specific embodiment of the present method, the subtraction hybridization is performed by PCR subtraction hybridization. The initiation of prostate regression may be performed by a number of means including surgical castration.

In one aspect of preparing such a prostate regression cDNA collection, the cDNA collection is prepared so as to be enriched in cDNAs for genes that are upregulated at a specific time-period during about the first 48 hours following the initiation of prostate regression. In one embodiment of this aspect of the invention, the mRNAs are collected at about the first 12 hours following the initiation of prostate regression. In another embodiment, the mRNAs are collected at about the first 24 hours following the initiation of prostate regression. In yet another embodiment, the mRNAs are collected at about 48 hours following the initiation of prostate regression.

In another aspect of preparing prostate regression cDNA collections of the present invention, the cDNA collection is prepared so as to be enriched in cDNAs for genes that are downregulated during a specific time-period the first 48 hours following the initiation of prostate regression. In one embodiment of this aspect of the invention, the mRNAs are collected at about the first 12 hours following the initiation of prostate regression. In another embodiment, the mRNAs are collected at about the first 24 hours following the initiation of prostate regression. In yet another embodiment the mRNAs are collected at about 48 hours following the initiation of prostate regression.

It is understood that all of the methods of preparing cDNA collections of the present invention may include a further step of combining two or more such collections to form yet another cDNA collection of the present invention. In one such embodiment, an upregulated cDNA collection obtained from cognate mRNAs collected at a selected timepoint and a corresponding downregulated cDNA collection, obtained from cognate mRNAs collected at an equivalent timepoint, are combined to form a cDNA collection of cDNAs encoding all such regulated proteins at the selected timepoint during prostate regression. In another such embodiment, a cDNA collection is formed by combining the upregulated cDNA collections obtained from cognate mRNAs collected at 12 hours, 24 hours and 48 hours respectively, following the initiation of prostate regression.

The present invention also includes the cDNA collections enriched in cDNAs for genes that are regulated at a selected time-period during the first 48 hours following the initiation of prostate regression, including genes that are regulated throughout the entire 48 hour time-period. All of the cDNA collections prepared by the methods of the present invention are included. In one particular aspect of the invention the cDNA collections are enriched in cDNAs for genes that are upregulated during the first 48 hours following the initiation of prostate regression. In another aspect of the invention the cDNA collections are enriched in cDNAs for genes that are downregulated during the first 48 hours following the initiation of prostate regression. In another particular embodiment, a cDNA collection comprises the upregulated cDNA collections obtained from cognate mRNAs collected at 12 hours, 24 hours, and 48 hours respectively, following the initiation of prostate regression. In yet another particular embodiment, a cDNA collection comprises the downregulated cDNA collections obtained from cognate mRNAs collected at 12 hours, 24 hours, and 48 hours respectively, following the initiation of prostate regression. In still another embodiment, a cDNA collection comprises cDNAs from cognate mRNAs that are up-regulated between 12 and 24 hours following the initiation of prostate regression.

In preferred embodiments of the regulated cDNA collections of the present invention, the cDNA collection does not contain a detectable glyceraldehyde phosphate dehydrogenase cDNA, as demonstrated with a labeled oligonucleotide probe that hybridizes with the glyceraldehyde phosphate dehydrogenase cDNA.

The present invention includes an upregulated prostate regression cDNA collection which hybridizes with one or more oligonucleotide probe or PCR primer derived from the sequences of SEQ ID NOs: 1–14. In a preferred embodiment, the upregulated prostate regression cDNA collection hybridizes with at least fourteen different oligonucleotide probes or PCR primers, each of which is derived from a different corresponding sequence of SEQ ID NOs: 1–14. In another preferred embodiment the upregulated prostate regression cDNA collection hybridizes to a collection of labeled DNA probes corresponding to +10 cDNA (upregulated cDNA collection) as deposited with the ATCC on Nov. 20, 1996 and assigned accession no. 97807. In yet another preferred embodiment of this type, the upregulated prostate regression cDNA collection does not detectably hybridize to a collection of labeled DNA probes corresponding to –8 cDNA (downregulated cDNA collection) as deposited with the ATCC on Nov. 20, 1996 and assigned accession no. 97808. In a more preferred embodiment, the upregulated prostate regression cDNA collection has two of the above properties. In the most preferred embodiment, the upregulated prostate regression cDNA collection has all of these properties.

In yet another aspect of the present invention, an upregulated prostate regression cDNA collection is prepared by a process comprising of initiating prostate regression in a animal having a prostate and then collecting mRNAs from the prostate within about the first 48 hours following the initiating of prostate regression. The cognate cDNAs are prepared from the mRNAs and subtraction hybridization is performed on the cognate cDNAs. The prostate regression cDNA collection prepared is enriched in cDNAs for genes that are upregulated during about the first 48 hours following the initiation of prostate regression. In preferred embodiments of this type, the method of initiating prostate regression in the animal is performed by castrating the animal. In other preferred embodiments of this type, the subtraction hybridization performed is PCR subtraction hybridization.

In still another preferred embodiments of this type, the upregulated prostate regression cDNA collection does not contain a detectable glyceraldehyde phosphate dehydrogenase cDNA, as demonstrated with a labeled oligonucleotide probe that hybridizes with the glyceraldehyde phosphate dehydrogenase cDNA. In a more preferred embodiment, the upregulated prostate regression cDNA collection further comprises cDNAs having sequences of SEQ ID NOs: 1–14. In the most preferred embodiment of this type the upregulated prostate regression +10 cDNA collection has ATCC no. 97807.

The present invention also includes a prostate regression cDNA collection enriched in cDNAs coded by genes that are downregulated during the first 48 hours following the initiation of prostate regression. In one embodiment the downregulated prostate regression cDNA collection does not contain a detectable glyceraldehyde phosphate dehydrogenase cDNA, as demonstrated with a labeled oligonucleotide probe that hybridizes with the glyceraldehyde phosphate dehydrogenase cDNA.

In another preferred embodiment, a downregulated prostate regression cDNA collection hybridizes to a collection of labeled DNA probes corresponding to −8 cDNA (downregulated cDNA collection) as deposited with the ATCC on Nov. 20, 1996 with assigned accession no. 97808. In yet another preferred embodiment of this type, the downregulated prostate regression cDNA collection does not detectably hybridize to a collection of labeled DNA probes corresponding to +10 cDNA (upregulated cDNA collection) as deposited with the ATCC on Nov. 20, 1996 with assigned accession no. 97807. In still another preferred embodiment of this type, the downregulated prostate regression cDNA collection contains a cDNA having the sequence SEQ ID NO: 15. In a more preferred embodiment, the downregulated prostate regression cDNA collection has two of these properties. In the most preferred embodiment the downregulated prostate regression cDNA collection has all of these properties.

In still another aspect of the present invention, a downregulated prostate regression cDNA collection is prepared by a process comprising of initiating prostate regression in a animal having a prostate and then collecting mRNAs from the prostate within about the first 48 hours following the initiating of prostate regression. The cognate cDNAs are prepared from the mRNAs and subtraction hybridization is performed on the cognate cDNAs. The prostate regression cDNA collection prepared is enriched in cDNAs for genes that are downregulated during about the first 48 hours following the initiation of prostate regression. In preferred embodiments of this type, the method of initiating prostate regression in the animal is performed by castrating the animal. In other preferred embodiments of this type, the subtraction hybridization performed is PCR subtraction hybridization.

In still another preferred embodiments of this type, the downregulated prostate regression cDNA collection does not contain a detectable glyceraldehyde phosphate dehydrogenase cDNA, as demonstrated with a labeled oligonucleotide probe that hybridizes with the glyceraldehyde phosphate dehydrogenase cDNA. In a more preferred embodiment, the downregulated prostate regression cDNA collection further comprises cDNAs having a sequence comprising SEQ ID NO: 15. In the most preferred embodiment of this type, the downregulated prostate regression cDNA collection has ATCC no. 97808.

The present invention also includes methods of using the cDNA collection of the present invention. In one such embodiment, an entire cDNA collection, such as the +10cDNA collection, ATCC no. 97807, is prepared as a labeled probe by PCR and used to identify prostate tissue undergoing programmed cell death. The tissue is obtained from patients where such a condition is suspected. In another such embodiment, the cDNA collection is used to identify genes likely to be involved in malignant prostate tissue. In another such embodiment, an entire cDNA collection, such as the −8cDNA collection, ATCC no. 97808, is prepared as a labeled probe by PCR and used to identify prostate tissue undergoing programmed cell death. The tissue is obtained from patients where such a condition is suspected. In another such embodiment, the cDNA collection is used to identify genes likely to be turned off in malignant prostate tissue.

The present invention also includes nucleic acids comprising the cDNAs of the present invention. In one embodiment the nucleic acid consists of a cDNA of the present invention and a heterologous nucleotide sequence. Another embodiment consists of a nucleic acid of 18 nucleotides or more that hybridizes with a cDNA of the present invention. In preferred embodiments the hybridization is performed under standard hybridization conditions. In a related aspect of the present invention consists of labeled oligonucleotide probes that hybridize with the cDNAs of the present invention. In preferred embodiments the hybridization is performed under standard hybridization conditions.

In particular embodiments an isolated nucleic acid comprises the nucleotide sequence of SEQ ID NO: 2, or 3, or 5, or 6, or 7, or 8, or 9, or 11, or 12, or 13, or 14, or 15. Corresponding nucleic acids consisting of the nucleotide sequence of SEQ ID NO: 2, or 3, or 5, or 6, or 7, or 8, or 9, or 11, or 12, or 13, or 14, or 15, and a heterologous nucleotide sequence are also part of the present invention. In addition, the present invention includes a nucleic acid of 18 nucleotides or more that hybridizes with a nucleic acid consisting of the nucleotide sequence of SEQ ID NO: 2, or 3, or 5, or 6, or 7, or 8, or 9, or 11, or 12, or 13, or 14, or 15, under standard hybridization conditions. A related embodiment includes a labeled oligonucleotide probe that hybridizes with a nucleic acid consisting of the nucleotide sequence of SEQ ID NO: 2, or 3, or 5, or 6, or 7, or 8, or 9, or 11, or 12, or 13, or 14, or 15, under standard hybridization conditions.

BRIEF DESCRIPTION OF THE DRAWINGS

FIG. 1A depicts the cDNA enrichment of the (+) and (−) collections as demonstrated by hybridization to labeled −8 cDNA (ATCC no. 97808). FIG. 1B depicts the plus cDNA enrichment as demonstrated by SGP2 hybridization. FIG. 1C depicts the removal of housekeeping cDNAs as demonstrated by GAPDH hybridization.

FIG. 6A–D. Cell Death in Regressing Prostate. In situ end labeling (Tunel) of dying cells in regressing prostate at time 0 (control) or 24, or 48 hours after inducing prostate regression. FIGS. 6A, 6B, 6C, and 6D represent increased magnification.

FIG. 7A–D. All Prostatic Epithelial Cells Respond to Changing Hormone Levels. In situ hybridization analysis of selected clones during prostate regression. FIG. 7A is for clone 15.85; FIG. 7B is clone pBK4; FIG. 7C is for clone pBK14; and FIG. 7D is for clone 10.17.

FIG. 8A–C. Genes Regulated as a Consequence of Programmed Cell Death. FIGS. 8A, 8B, and 8C depict in situ hybridization of mRNAs 10.17, 10.1, and 10.3 respectively at the noted times.

DETAILED DESCRIPTION OF THE INVENTION

Figure 1:
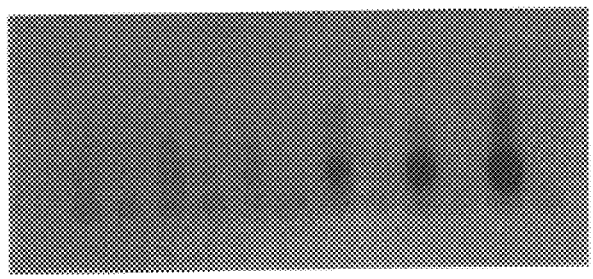
FIGS. 1A–C. Enrichment of plus (upregulated) and minus (downregulated) cDNA by subtractive hybridization.
Figure 1:
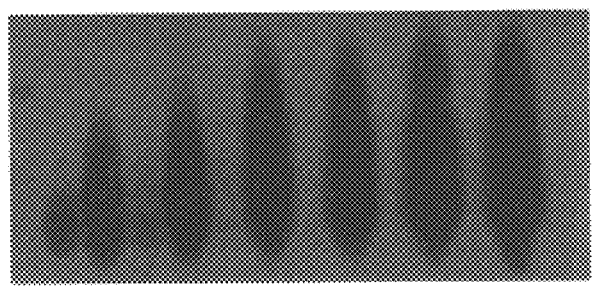
Figure 1:
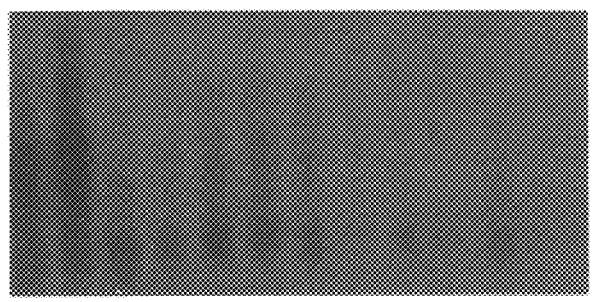

The present invention in its broadest aspect identifies additional cellular components involved in either prostate homeostasis and prostate regression, as well as those involved generally in programmed cell death.

In one aspect of the present invention are cDNA collections that are significantly enriched with nucleic acids encoding proteins that are regulated during prostate regression. These novel cDNA collections provide a rich resource for the initiation of molecular and genetic studies of prostate cell growth and death, and for the identification of new molecules involved in the programmed cell death pathway. In one embodiment of this type, the cDNAs are placed in arrays of multiple sampling chambers and mixed with mRNAs collected from a patient having a diseased or dysfunctional prostate condition in order to identify specific mRNAs encoding proteins involved in the diseased or dysfunctional condition.

In another aspect of the invention, particular cDNA transcripts are described that encode proteins that are either unique to general programmed cell death or unique to prostate regression. These transcripts can be used as markers to monitor and/or to diagnose such conditions. In yet another aspect of the invention, methods of subtraction hybridization are employed to prepare cDNA libraries that are highly enriched in clones whose cognate mRNAs are strongly regulated during programmed cell death such as during prostate regression.

Prior to the present invention no cDNA collection existed that was significantly enriched for genes regulated during prostate regression. An earlier attempt had been made by preparing a cDNA library eight days following castration in which of the 4400 clones analyzed only 0.8% were found to be regulated [Leger et al., *Biochem. Biophy. Res. Comm.* 147:196–203 (1987).] In contrast, in a representative DNA collection of the present invention, based on the sequence analysis of 22 different sequences (from a group 30 randomly selected clones) nineteen of the twenty two clones (86%) were enriched during the cycles of subtractive hybridization indicating that they encoded regulated proteins. Therefore, prior to the present invention, the individual proteins encoded by the cDNA collections of the present invention could only be identified on an individual basis, with each identification requiring its own specialized protocol, since no such enriched source of cDNA encoding proteins regulated during prostate regression existed.

Each of the components of the cDNA collections can be used either as probes or primers to obtain full-length homologues of nucleic acids encoding proteins that are regulated during programmed cell death, including human homologues. Each cDNA in the upregulated cDNA collections also may be used as a general probe to detect cells suspected of undergoing apoptosis. One such general cDNA is 10.27 (SEQ ID NO:11). In an alternative embodiment, general apoptosis is monitored with cDNA 10.28, (SEQ ID NO:12). In other cases, a cDNA of the present invention may be used as a probe to detect cells suspected of undergoing prostate regression. Such probes can be used either alone or in combination with other cDNAs in the upregulated cDNA collection. In one embodiment where prostate regression is being monitored, the cDNA is 10.3, (SEQ ID NO:2). In another such embodiment, the cDNA is 10.30 (SEQ ID NO:14). In related embodiments, the cDNA is SEQ ID NO:3, or SEQ ID NO:5, or SEQ ID NO:6, or SEQ ID NO:7, or SEQ ID NO:8, or SEQ ID NO:9, or SEQ ID NO:11, or SEQ ID NO:13.

Oligonucleotide probes made from any of these nucleotide sequences (e.g., nucleotide fragments of the disclosed sequences) can also be used for a similar purpose. In addition, oligonucleotide probes that hybridize under standard hybridization conditions with the cDNAs can also be used for this purpose. Furthermore, any of these probes, can be labeled and/or contain a heterologous nucleotide sequence.

In a preferred embodiment two cDNAs, such as 10.3 and 10.30 are used. In a more preferred embodiment of this type the entire +10 cDNA collection, (Example, infra) as deposited on Nov. 20, 1996 with the American Type Culture Collection, 12301 Parklawn Drive, Rockville, Md. 20852, USA, and assigned accession no. 97807 may be used as a combined probe.

Similarly a cDNA in the downregulated cDNA collection can used as a probe to identify the factors missing in cells that will not die, such as cancer cells, and thereby aid in its diagnosis. One specific example is a T-cell lymphoma, which does not follow the fate of normal T-cells by dying under a programmed cell death pathway. One such embodiment is a nucleic acid comprising the nucleotide sequence of SEQ ID NO:15. An oligonucleotide probe prepared from this nucleotide sequence can also be used for a similar purpose, as can an oligonucleotide probe that hybridizes under standard hybridization conditions with the cDNA. In addition, such probes can be labeled and/or contain a heterologous nucleotide sequence. In a preferred embodiment, the entire –8 cDNA collection, (Example, infra) as deposited on Nov. 20, 1996 with the American Type Culture Collection, 12301 Parklawn Drive, Rockville, Md. 20852, USA, and assigned accession no. 97808 may be used as a combined probe.

cDNA collections were deposited with the ATCC under the foregoing provisions of the Budapest Treaty for the Deposit of Microorganisms for Patent Purposes. The +10cDNA collection was registered under the designation cDNA JG+10 (Accession no. 97807) and the –8 cDNA collection was registered under the designation cDNA JG-8 (Accession no. 97808).

One embodiment of the present invention is a cDNA collection that has a majority of its cDNAs encoding mRNAs that are greatly enriched in normal or regressing prostate, suggesting that they have a specific role in prostate physiology. On the other hand, approximately 5–10% of the encoded mRNAs are also expressed in dying cells during tissue remodeling in response to other stimuli, or in cells undergoing programmed cell death during development, indicating that 5–10% of the cDNAs have a direct role in a general cell-death pathway. In addition approximately 75% of the identified cDNAs encode nucleic acid transcripts that are either uncharacterized or correspond to expressed sequence tags having unknown functions. A significant number of these cDNAs identify new members of existing gene families for which finctional data is available.

In another aspect of the invention, methods of subtraction hybridization are employed to prepare cDNA libraries that are highly enriched in clones whose cognate mRNAs are strongly regulated during programmed cell death, such as during prostate regression. These methods rely on the temporal progression in the expression of genes regulated in programmed cell death. As a general rule, mRNAs are collected at or prior to the peak of the degradation of DNA associated with the apoptosis. Thus in the embodiment described in the Example, infra, RNA preparations from 12, 24, and 48 hours following castration of a male rat are used for the subtractive hybridization procedure because DNA degradation peaked at 48 hours after castration.

In specific embodiments of the present invention, the subtractive hybridization is performed by PCR. The PCR based subtraction hybridization comprises the use of tester cDNA and driver cDNA. In the construction of a cDNA collection for genes upregulated during prostate regression, the tester cDNA initially comprises the cDNA cognate to the mRNA isolated from a subject animal at a chosen time point after initiating prostate regression. The cDNA cognate to the mRNA obtained from a corresponding control animal is used as the driver cDNA. The cDNA in common between the tester cDNA and the driver cDNA is progressively subtracted out from the tester cDNA through progressive rounds of PCR. In preferred embodiments of this type, the driver cDNA is used to remove essentially all of the DNA sequences that are common to both the driver cDNA and the tester cDNA. The remaining cDNA in the tester cDNA represents the cognate mRNA that was upregulated.

On the other hand, in the construction of a cDNA collection for genes downregulated during prostate regression, the tester cDNA initially comprises the cDNA cognate to the mRNA isolated from a control animal whereas the driver cDNA is cognate to the mRNA obtained from a subject animal at the chosen time point after initiating prostate regression. The cDNA in common between the tester cDNA and the driver cDNA is again progressively subtracted out from the tester cDNA through progressive rounds of PCR. Again, in preferred embodiments of this type the driver cDNA is used to remove essentially all of the sequences that are common to the driver cDNA and the tester cDNA. However, in this case the remaining cDNA in the tester cDNA represents the cognate mRNA that was downregulated.

As is readily apparent, any two mRNA collections may be used to generate a corresponding pair of cDNA collections that can be used as either the tester or the driver. The present invention includes the selection of mRNAs collected at any two time points throughout the time-course of a cell undergoing programmed cell death to generate a cDNA collection of the present invention, and thus includes a large number of unique cDNA collections generated through employing driver cDNA and the corresponding tester cDNA obtained from mRNA collections collected at any two selected time points. In preferred embodiments of the present invention, one of the time points selected is equal to or earlier than the time point that corresponds to the peak time of apoptotic DNA degradation. In one such embodiment, the tester cDNAs are cognate to mRNAs collected at the time of peak DNA degradation and the driver cDNAs are cognate to the mRNAs collected at a time when the programmed cell death is essentially complete. In another such embodiment, the tester cDNAs are cognate to mRNAs collected prior to the initiation of programmed cell death and the driver cDNAs are cognate to the mRNAs collected at the time of peak DNA degradation.

The mRNA from several time points may be pooled together to form the tester or driver cDNA. For example mRNA collected at 12, 24 and 48 hours after castration of a rat may be pooled together and used to generate the tester cDNA, whereas the driver cDNA may be obtained from mRNA collected from a control animal or when appropriate, the subject animal prior to being induced to undergo programmed cell death.

In such embodiments the PCR based subtractive hybridization is repeated with the same driver over multiple rounds. The number of rounds necessary to obtain a useful cDNA collection depends on a number of factors including the source of mRNA, the intended use of the cDNA collection, the difference in content between the tester cDNA and the driver cDNA, and the ratio between the amount of driver and tester cDNA used.

In one embodiment, an upregulated cDNA collection is constructed by performing 8 rounds of PCR subtraction hybridization using a 20-fold excess of driver cDNA. In yet another embodiment, a downregulated cDNA collection is constructed by performing 8 rounds of PCR subtraction hybridization using a 20-fold excess of driver cDNA (–8 cDNA, Accession no. 97808).

In certain instances a particular cDNA will be found to be disproportionately represented in a cDNA collection generated by subtractive hybridization. Such a situation can leading to the effective masking of the majority of other cDNAs having a significantly lower concentration in the cDNA collection. In such instances this particular cDNA can be used as the driver and the cDNA collection so generated (for example a +8cDNA for an upregulated cDNA collection after eight rounds of subtractive hybridization) may be used as the tester cDNA. In one such embodiment exemplified in the Example, infra, after two additional rounds of subtractive hybridization with the particular cDNA as the driver, effectively removed from the masking effect of that cDNA on the cDNA collection generated (+10 cDNA, Accession no. 97808).

The cDNA collections can be obtained from practically any animal source including humans. Appropriate animals include primates, rats, mice, rabbits, goats, sheep, pigs, dogs, cats, avian species, such as chickens and turkeys. In one particular embodiment, human tissue is obtained during a transsexual operation in which a males surgically changed to become a female.

Therefore, if appearing herein, the following terms shall have the definitions set out below.

As used herein a "cDNA collection" is a collection of cDNAs that are obtained from cognate mRNAs collected from a particular type of tissue (e.g., prostate tissue) at a particular time (i.e., a control sample or at some time during or after the progression in a cell of programmed cell death.) The cDNA collection may be maintained as an isolated group of nucleic acids or it may be included in a group of vectors containing the cDNAs, such as in a phage library. Thus, as used herein, the cDNAs of the present invention are generally referred to as part of cDNA collections since they may be stored as a collection of isolated nucleic acids, even though they also may be placed in a cDNA library. Therefore, the two terms, cDNA collection and cDNA library, are used interchangeably herein, to describe the same group of cDNAs.

As used herein, a cDNA collection is "enriched in cDNA" for cognate mRNAs having a particular characteristic (such as those regulated during prostate regression) when greater than about 20% to 40% of the cDNAs in a random sampling of about 20 to 30 cDNAs of the cDNA collection, correspond to cognate mRNAs that have the particular characteristic, e.g., being regulated during prostate regression. In a preferred embodiment, greater than about 40% to 60% of the cDNAs in a random sampling of a cDNA collection correspond to cognate mRNAs that have the particular characteristic. In a more preferred embodiment greater than 80% to 95% of the cDNAs in a random sampling of a cDNA collection correspond to cognate mRNAs that have the particular characteristic. In the most preferred embodiment of the present invention, 100% of the cDNAs in a random sampling of an enriched cDNA collection correspond to cognate mRNAs that have the particular characteristic.

As used herein the terms "programmed cell death", and "apoptosis" are used interchangeably. In the absence of testosterone, programmed cell death is triggered in the prostate and the prostate dies; a surgically castrated mammal is an experimental animal model for programmed cell death of the prostate.

As used herein, "initiation of prostate regression" signifies the point in time when an event that leads to prostate regression is induced. For example, the removal of the testes initiates prostate regression when induced by surgical castration.

As used herein "genes that are regulated" during prostate regression include all prostate genes that are significantly attenuated during prostate regression. Significant attenuation encompasses at least a 2–4 fold increase or decrease in the level of a particular mRNA collected at a designated timepoint over the corresponding level of the particular mRNA collected during some earlier timepoint, e.g., the basal state. A regulated gene may be initially upregulated and subsequently downregulated during the progression of prostate regression. Similarly, a regulated gene may be initially downregulated and subsequently upregulated during the progression of prostate regression. On the other hand, a regulated gene may also be upregulated or in the alternative, downregulated throughout the progression of prostate regression.

As used herein cDNA of "genes that are upregulated" are cDNA from cognate mRNA of genes that are positively regulated during prostate regression. Such positive regulation encompasses at least a 2–4 fold increase in the level of a particular mRNA collected at a designated timepoint over the corresponding level of the particular MRNA collected during an earlier timepoint, e.g., the basal state. In a specific embodiment, an upregulated gene is not detectably expressed until initiation of regression.

As used herein cDNA of "genes that are downregulated" are cDNA from cognate mRNA of genes that are negatively regulated during prostate regression. Such negative regulation encompasses at least a 2–4 fold decrease in the level of a particular mRNA collected at a designated timepoint over the corresponding level of the particular mRNA collected during the basal state. In a specific embodiment, an downregulated gene is not detectably expressed after initiation of regression.

As used herein "at about" indicates within 15–20% of the quantity listed. For example, about the first 12 hours means between the first 10 to 14 hours.

Subtractive Hybridization

Subtractive hybridization is a method that can be used for the identification and isolation of the genes that are induced or suppressed in response to prostate regression. Subtractive hybridization is particularly useful for selectively cloning the nucleotide sequences present in one DNA population, but absent in another.

The selective cloning is accomplished by generating single stranded cDNA libraries from both the control prostate tissue, for example and tissue obtained during or after prostate regression. In one example of this methodology, the tissue obtained during or after prostate regression is the tester cDNA and the control tissue is the driver cDNA. Generally the driver cDNA is derivatized, such as with biotin, so that it can be selectively isolated (with strep avidin in this case). The two cDNA libraries are denatured and the driver cDNA is hybridized with the tester cDNA. This results in heteroduplex formation between the nucleotide sequences that the driver cDNA library and the tester cDNA library have in common. The common nucleotide sequences, i.e., the sequences that form heteroduplexes, and the single stranded driver cDNA can be selectively removed, thereby enriching the remaining non-hybridized single-stranded tester cDNA. The remaining single-stranded nucleotide sequences are enriched for the ones present in the tester cDNA library but not the driver cDNA library. The resulting tester cDNA can then be mixed again with fresh driver cDNA and the process can be repeated as many times as required.

Subtractive hybridization has led to the discovery of many important genes including the myogenesis differentiation marker MyoD1, the T-cell receptor and genes activated at the gastrulation stage of *Xenopus laevis* [Davis et al., *Cell*, 51:987–1000 (1987]; [Hedrick et al., *Nature*, 308:149–153 (1984)]; [Sargent et al., *Science*, 222:135–139 (1983)].

The power of the subtractive library method has been significantly enhanced by the polymerase chain reaction (PCR), which allows performance of multiple cycles of hybridization using small amounts of starting material [Wieland et al., *Proc. Natl, Acad. Sci. USA*, 87:2720–2724 (1990)]; [Wang et al., *Proc. Natl. Acad. Sci. USA*, 88:11505–11509 (1991)]; [Cecchini et al., *Nucleic Acids Res.*, 21:5742–5747 (1993)].

In one embodiment PCR-driven subtraction hybridization uses biotinylated driver DNA as has been performed to identify differentially expressed genes [Lebeau et al., *Nucleic Acids Res.*, 19:4778 (1991)]; [Duguid et al., *Nucleic Acids Res.*, 18:2789–2792 (1990)]. In another related embodiment, the PCR subtractive hybridization is performed by the method of enzymatic degrading subtraction hybridization [Zeng, J. *Enzymatic Degrading Subtraction Hybridization*, U.S. Pat. No. 5,525,471, Issued Jun. 11, 1996, hereby incorporated by reference in its entirety].

Genes Encoding Proteins That Are Regulated During Prostate Regression

The present invention contemplates isolation of a gene encoding a protein regulated during prostate regression, including a full length, or naturally occurring form of such a prostate protein, and any antigenic fragments thereof from any animal, particularly mammalian and more particularly human, source. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A*

*Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" is a nucleotide sequence that is not part of the coding sequence of a nucleic acid in the natural cellular environment of the nucleic acid, but has been combined with the nucleic acid by recombinant methods. For example, a nucleic acid consisting of a nucleotide sequence of the present invention and a heterologous nucleotide sequence is part of the present invention. In one embodiment of this type, the heterologous nucleotide sequence has a regulatory and/or structural property. In another such embodiment the heterologous nucleotide function as a means of detecting the nucleotide sequences of the present invention.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 18 nucleotides. Preferably a minimum length for a hybridizable nucleic acid is at least about 24 nucleotides; more preferably at least about 6 nucleotides; and most preferably the length is at least about 48 nucleotides. As used in his context at least "about" means plus or minus 12.5%, e.g., at least about 18 nucleotides, as a lower limit of at least 16 nucleotides, and an upper limit of at least 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

An homologous gene encoding a protein that is regulated during prostate regression, whether genomic DNA or cDNA, can be isolated from any source, particularly from a human cDNA or genomic library. Methods for obtaining such prostate protein gene homologues are well known in the art, (see, e.g., Sambrook et al., 1989, supra). In particular, the use of the cDNA collections of the present invention as specific probes and/or templates for probes to obtain such homologous nucleic acids are envisioned by the present invention.

Accordingly, a cell from a prostate of any animal potentially can serve as the nucleic acid source for the molecular cloning of such a regulated prostate protein gene homologue. The DNA may be obtained by standard procedures known in the art from cloned DNA (e.g., a DNA "library"), and preferably is obtained from a cDNA library prepared from tissues with high level expression of the protein (e.g., a prostate epithelial cDNA library), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAs in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired prostate protein gene may be accomplished in a number of ways. For example, if an amount of a portion of a prostate protein gene or its specific RNA, or a fragment thereof, is available and can be purified and labeled, the generated DNA fragments may be screened by nucleic acid hybridization to the labeled probe [Benton and Davis, Science, 196:180 (1977)]; [Grunstein and Hogness, Proc. Natl. Acad. Sci. U.S.A., 72:3961 (1975)]. For example, a set of oligonucleotides corresponding to the partial amino acid sequence information obtained for the prostate protein can be prepared and used as probes for DNA encoding prostate protein, as was done in a specific example, infra, or as primers for cDNA or mRNA (e.g., in combination with a poly-T primer for Reverse Transcriptase-Polymerase Chain Reaction, RT-PCR). Preferably, a fragment is selected that is highly unique to a regulated prostate protein of the invention. Those DNA fragments with substantial homology to the probe will hybridize. As noted above, the greater the degree of homology, the more stringent hybridization conditions can be used. In a specific embodiment, stringency hybridization conditions are used to identify an homologous prostate protein gene.

Further selection can be carried out on the basis of the properties of the gene, e.g., if the gene encodes a protein product having the isoelectric, electrophoretic, amino acid composition, or partial amino acid sequence of prostate protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophorese is behavior, proteolytic digestion maps, or antigenic properties as known for the regulated prostate protein.

A gene encoding a regulated prostate protein of the present invention can also be identified by mRNA selection, i. e., by nucleic acid hybridization followed by in vitro translation. In this procedure, nucleotide fragments are used to isolate complementary mRNAs by hybridization. Such DNA fragments may represent available, purified prostate protein DNA, or may be synthetic oligonucleotides designed from the partial amino acid sequence information. Immunoprecipitation analysis or functional assays of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a prostate protein.

Labels. A radiolabeled cDNA encoding a regulated prostate protein of the present invention can be synthesized using the selected mRNA (from the adsorbed polysomes) as a template. The radiolabeled mRNA or cDNA may then be used as a probe to identify homologous prostate protein DNA fragments from among other genomic DNA fragments.

Similarly all of the nucleic acids of the present invention can be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

Solid supports for binding the nucleic acids of the present invention. The nucleic acids of the present invention, either labeled or not may be placed onto a solid support e.g., for greater ease of separation from large concentrations of potential binding partners. A solid phase support for use in the present invention will be inert to the reaction conditions for binding. A solid phase support for use in the present invention must have reactive groups in order to attach a binding partner, such as an nucleic acid obtained from a cDNA collection of the present invention. In another embodiment, the solid phase support may be also useful as chromatographic support, such as the carbohydrate polymers SEPHAROSE, SEPHADEX, agarose. As used herein, a solid phase support is not limited to a specific type of support. Rather a large number of supports are available and are known to one of ordinary skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.). In synthesis of oligonucleotides, a silica based solid phase support may be preferred. Silica based solid phase supports are commercially available (e.g., from Peninsula Laboratories, Inc.; and Applied Biosystems, Inc.).

Expression of Prostate Proteins Regulated During Prostate Regression

The nucleotide sequence coding for a regulated prostate protein, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a regulated prostate protein of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding prostate protein and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant prostate protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell containing the recombinant vector comprising a nucleic acid encoding a regulated prostate protein of the present invention is cultured in an appropriate cell culture medium under conditions that provide for expression of the corresponding prostate protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a regulated prostate protein may be controlled by any promoter/enhancer element known in the art, but these regulatory elements must be functional in the host selected for expression. Promoters which may be used to control prostate protein gene expression include, but are not limited to, the SV40 early promoter region [Benoist and Chambon, *Nature*, 290:304–310 (1981)], the promoter contained in the 3' long terminal repeat of Rous sarcoma virus [Yamamoto et al., *Cell*, 22:787–797 (1980)], the herpes thymidine kinase promoter [Wagner et al., *Proc. Natl. Acad. Sci. U.S.A.*, 78:1441–1445 (1981)], the regulatory sequences of the metallothionein gene [Brinster et al., *Nature*, 296:3942 (1982)]; prokaryotic expression vectors such as the P-lactamase promoter [Villa-Kamaroff et al., *Proc. Natl. Acad. Sci. U.S.A.*, 75:3727–3731 (1978)], or the tac promoter [DeBoer et al., *Proc. Natl. Acad. Sci. U.S.A.*, 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell*, 38:639–646 (1984)]; [Ornitz et al., *Cold Spring Harbor Symp. Quant. Biol.*, 50:399–409 (1986)]; [MacDonald, *Hepatology*, 7:425–515 (1987)]; insulin gene control region which is active in pancreatic beta cells [Hanahan, *Nature*, 315:115–122 (1985)], immunoglobulin gene control region which is active in lymphoid cells [Grosschedl et al., *Cell*, 38:647–658 (1984)]; [Adames et al., *Nature*, 318:533–538 (1985)]; [Alexander et al., *Mol. Cell. Biol.*, 7:1436–1444 (1987)], mouse mammary tumor virus control region which is active in testicular, breast, lymphoid and mast cells [Leder et al., *Cell*, 45:485–495 (1986)], albumin gene control region which is active in liver [Pinkert et al., *Genes and Devel.*, 1:268–276 (1987)], alpha-fetoprotein gene control region which is active in liver [Krumlauf et al., *Mol. Cell. Biol.*, 5:1639–1648 (1985)]; [Hammer et al., *Science*, 235:53–58 (1987)], alpha 1-antitrypsin gene control region which is active in the liver [Kelsey et al., *Genes and Devel.*, 1:161–171 (1987)], beta-globin gene control region which is active in myeloid cells [Mogram et al., *Nature*, 315:338–340 (1985)]; [Kollias et al., *Cell*, 46:89–94 (1986)], myelin basic protein gene control region which is active in oligodendrocyte cells in the brain [Readhead et al., *Cell*, 48:703–712 (1987)], myosin light chain-2 gene control region which is active in skeletal muscle [Sani, *Nature*, 314:283–286 (1985)], and gonadotropic releasing hormone gene control region which is active in the hypothalamus [Mason et al., *Science*, 234:1372–1378 (1986)].

Expression vectors containing a nucleic acid encoding a regulated prostate protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a regulated prostate protein is inserted within the "selection marker" gene sequence of the vector, recombinants containing the prostate protein insert can be identified by the absence of the prostate protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., *Gene*, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglIII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with 5 inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the prostate protein. For example, the non-fusion pYES2 vector (XbaI, SphI, ShoI, NotI, GstXI, EcoRI, BstXI, BamH1, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, a transmembrane regulated prostate protein of the present invention that is expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, prostate protein activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990).

A recombinant marker protein expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P40 (NP40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

Gene Targeting

One key aspect of the present invention is the use of the cDNA collections described herein for identifying key proteins involved in cell homeostasis, and in the alternative, key proteins involved in programmed cell death. In the former case, any cDNA collection that is enriched in cDNAs for genes that are downregulated at a selected time during the first 48 hours following the initiating of prostate regression, including genes that are downregulated throughout the entire 48 time-period may be used, whereas in the latter case a cDNA collection that is enriched in cDNAs for genes that are upregulated during the first 48 hours following the initiates of prostate regression is used. In either case, using techniques described herein, and as well those well known in the art, the appropriate gene can be selected.

In one such example, the functional activity of a protein regulated during prostate regression that has been identified through the use of a cDNA collection of the present invention, can be evaluated transgenically. In this respect, a transgenic animal model can be used. The gene for such a regulated protein can be used in complementation studies employing a transgenic animal. Transgenic vectors, including viral vectors, or cosmid clones (or phage clones) corresponding to the wild type locus of a candidate gene, can be constructed using the isolated prostate gene. Cosmids may be introduced into transgenic mice using published procedures [Jaenisch, Science, 240:1468–1474 (1988)]. In a genetic sense, the transgene acts as a suppressor mutation. In preferred embodiments of all transgenic animals of the present invention, the transgenic animal is a mouse.

Alternatively, a transgenic animal model can be prepared in which the gene encoding a protein regulated during prostate regression that is inducibly expressed, is now disrupted. Gene expression is disrupted, according to the invention, when no functional protein is expressed. One standard method to evaluate the phenotypic effect of a gene product is to employ knock-out technology to delete the gene. Alternatively, recombinant techniques can be used to introduce mutations, such as nonsense and amber mutations, or mutations that lead to expression of an inactive protein.

As used herein "Gene targeting" is a type of homologous recombination that occurs when a fragment of genomic DNA is introduced into a mammalian cell and that fragment locates and recombines with endogenous homologous sequences.

As used herein a "knockout animal" is an animal that contains within its genome a specific gene that has been inactivated by the method of gene targeting. A knockout animal includes both the heterozygote animal (i.e., one defective allele and one wild-type allele) and the homozygous mutant (i.e., two defective alleles). In a preferred embodiments of the present invention the knockout animal is a mouse.

As used herein a "marker gene" is a selection marker that facilitates the isolation of rare transfected cells from the majority of treated cells in the population. A non-comprehensive list of such markers includes neomycin phosphotransferase, hygromycin B phosphotransferase, Xanthine/guanine phosphoribosyl transferase, herpes simplex thymidine kinase, and diphtheria toxin.

Gene targeting in embryonic stem cells is a relatively new technique that allows the precise manipulation of genes in vivo. This technique allows the creation of animals, e.g., mice with defined mutations in the structure of any given gene. This ability to generate predetermined mutations gives investigators the ability to apply the power of genetics to a complex human regulatory system, such as programmed cell death, as it has successfully been applied in neuronal systems for such organisms as Drosophila and C. elegans.

A key to finding treatments for many disorders has been the development of appropriate animal models. The present invention includes a knockout animal containing a non-functional allele for the gene that naturally encodes and expresses the functional form of a specific protein regulated during prostate regression. Included within this aspect of the invention is a knockout mouse containing two non-functional alleles for the gene that naturally encodes and expresses a functional form of a specific protein regulated during prostate regression, and therefore is unable to express a functional form of the specific protein.

Non-functional alleles can be generated in any number of ways that are well known in the art, all of which may be used in the present invention. In some embodiments, a non-functional allele is made defective by an insertion of extraneous DNA into the coding region of the allele of a particular protein that is regulated during prostate regression. In a preferred embodiment, the insertion is placed in the first exon of the coding region of the gene. In more preferred embodiments, the insertion contains a signal to terminate transcription prior to the transcription of a region of the allele that encodes the particular protein regulated during prostate regression. In these preferred embodiments it is still more preferred to remove a section of DNA at the beginning of the coding region for the regulated protein and replacing it with the above insertion.

The present invention includes a knockout animal that phenotypically possess a partially or fully regressed prostate. In such embodiments the gene that was purposely inactivated by a method described above, is identified through the use of a cDNA collection of the present invention that is enriched in cDNAs for genes that are downregulated during the first 48 hours following the initiating of prostate regression. In an alternative embodiment, a knockout animal is produced that can maintain a healthy prostate even in the presence of a drug that otherwise suppresses androgen expression in the corresponding wildtype animal. In such embodiments the gene that was purposely inactivated by a method described above, is identified through the use of a cDNA collection of the present invention that is enriched in cDNAs for genes that are upregulated during the first 48 hours following the initiating of prostate regression.

The phenotype of a knockout animal having a healthy or regressed prostate may be determined in a large number of ways that are well known in the art. In some embodiments this can be readily demonstrated by e.g., general physiological tests specific for prostate viability or by microscopy studies with prostate tissue and cell samples as shown in the Example, infra.

The present invention also includes a method for producing the knockout animal of the instant invention that includes: obtaining genomic DNA encoding a protein regulated during prostate regression, constructing a vector containing said genomic DNA and a marker gene wherein said marker gene is placed within the exon of said genomic DNA. The vector is then electroporated into an embryonic stem cell and an embryonic stem cell is selected that has integrated the vector into the genome, wherein the selected cell has integrated the marker gene into the endogenous site of the gene for a regulated prostate protein in the mouse genome. The cell is then injected into a mouse blastocyst which is then re-implanted into a pseudopregnant female mouse, which gives birth to a chimeric mouse containing a defective allele for the regulated prostate protein in its germ line. The chimeric mouse is then mated to a wildtype mate of a standard in-bred line to generate a heterozygous knock-out animal. Two heterozygous animals are then bred generating a homozygous knockout animal offspring.

Another aspect of the invention is a method for selecting a therapeutic agent for possible use as an inducer or inhibitor of programmed cell death which comprises administering a suspected therapeutic agent to the knockout animal of the present invention and measuring and/or determining the putative therapeutic agent's effect on any of the phenotypic characteristics which may be believed to be related to programmed cell death.

A suspected therapeutical agents may be obtained from any number of drug or peptide libraries including those commercially available from drug Chemical companies.

Uses of cDNA collections of the present invention to identify specific agonists and antagonists of programmed cell death. The present invention includes the identification and isolation of genes encoding a prostate protein regulated during prostate regression that are obtained through the use of the cDNA collections of the present invention. The present invention also provides for expression of that protein in quantities greater than can be isolated from natural sources, or in indicator cells that are specially engineered to indicate the activity of the protein expressed after transfection or transformation of the cells. Knowledge of the primary sequence of a particular protein encoded by a nucleic acid in a cDNA collection of the present invention, and the similarity of that sequence with proteins of known function, can provide an initial clue as in identifying specific agonists or antagonists of the protein. These sequence comparisons may be performed through the use of a variety of databases and available software search programs including GenBank, and the BLAST search program, EMBL, DDBJ, PIR, SWISS-PROT, PRF, PDB, UNIGENE, dbEST, GENESEQ, and ENZYMATE.

In addition, as described above, the regulated prostate protein may be rendered functionally inactive in a transgenic animal, such as a knockout mouse, or in the alternative placed in a cell, or tissue or even "knockin" animal that does not normally express the regulated prostate protein. Accordingly, in addition to rational design of agonists and antagonists based on the structure of the regulated prostate protein, the present invention contemplates an alternative method for identifying specific drugs that can either enhance or diminish the activity of such a regulated prostate protein using various screening assays known in the art. Such drugs have uses that either promote programmed cell death, such as in the fight against cancerous tumors for example, or inhibit cell death, such as in the prevention of an abnormal prostate regression.

Any screening technique known in the art can be used to screen for such drugs. The present invention contemplates screens for small molecule drugs or in the case where the regulated prostate protein is a receptor, ligand analogs and mimics, as well as screens for natural ligands that bind to and agonize or antagonize such a receptor in vivo. For example, natural products libraries can be screened using assays of the invention for molecules that naturally promote or inhibit programmed cell death in the prostate.

Identification and screening of potential drugs can be further facilitated by determining structural features of a regulated protein, e.g., using X-ray crystallography, neutron diffraction, nuclear magnetic resonance spectrometry, and other techniques for structure determination. These techniques provide for the rational design or identification of drugs that are either agonists and antagonists.

Drug libraries. An important approach for drug development uses recombinant bacteriophage to produce large libraries. Using the "phage method" [Scott and Smith, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for drugs that effect the regulation of the proteins encoded by the cDNA collections of the present invention.

More recent methods of screening and constructing such nucleotide and peptide libraries have been disclosed in Schatz et al., U.S. Pat. No. 5,498,530; Dower et al., U.S. Pat. No. 5,432,018; Kim et al., U.S. Pat. Nos. 5,382,513 and 5,510,240; and International Patent Publication No. WO 9534664, each of which is incorporated herein by reference in its entirety.

Antisense nucleic acids. An alternative procedure to knockout technology is to suppress the activity of an otherwise functional regulated prostate protein in an animal through antisense hybridization. Antisense nucleic acids are DNA or RNA molecules that are complementary to at least a portion of a specific mRNA molecule [see Marcus-Sekura, Anal. Biochem. 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells.

Antisense methods have been used to inhibit the expression of many genes in vitro [Marcus-Sekura, 1988, supra; Hambor et al., J. Exp. Med. 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids. This technique has been used to inhibit TK synthesis in tissue culture and to produce phenotypes of the Kruppel mutation in Drosophila, and the Shiverer mutation in mice Izant et al., *Cell,* 36:1007–1015 (1984); Green et al., *Annu. Rev. Biochem.,* 55:569–597 (1986); Katsuki et al., *Science,* 241:593–595 (1988). An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site. This transgene will be used to make transgenic mice, or by using gene knockout technology.

Purification of the regulated prostate proteins encoded by the nucleic acids of the present invention and homologues thereof:

Regulated proteins of the present invention and homologues thereof can be purified by any number of procedures that encompass a wide variety of known purification steps. Those with skill in the art would know to refer to references, such as the Methods of Enzymology series, for greater detail and breadth. Initial steps for purifying the proteins of the present invention include salting in or salting out, such as in ammonium sulfate fractionations; solvent exclusion fractionations, e.g., an ethanol precipitation; detergent extractions to free membrane bound proteins using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxy propyl] amino ethyl (QAE) Sephadex or cellulose; or with a cation exchanger such as carboxymethyl (CM) or sulfo propyl (SP) Sephadex or cellulose. Alternative means of solid phase binding includes the exploitation of hydrophobic interactions e.g., the using of a solid support such as phenylSepharose and a high salt buffer; affinity-binding, using, e.g., a regulated prostate protein bound to an activated support; immuno-binding, using e.g., an antibody to the a regulated prostate protein bound to an activated support; as well as other solid phase supports including those that contain specific dyes or lectins etc. A further solid phase support technique that is often used at the end of the purification procedure relies on size exclusion, such as Sephadex and Sepharose gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a biological buffer at a pH close to the pKa of that buffer. Typical buffers can be purchased from most biochemical catalogues and include the classical buffers such as Tris, pyrophosphate, monophosphate, and diphosphate, or the Good buffers [Good, N. E., et al., *Biochemistry,* 5:467 (1966)]; [Good, N. E. and Izawa, S., *Meth. Enymol.,* 24, Part B, 53 (1972)]; and [Fergunson, W. J. and Good, N. E., *Anal. Biochem.,* 104:300 (1980)] such as Mes, Hepes, Mops, tricine and Ches.

Materials to perform all of these techniques are available from a variety of sources such as Sigma Chemical Company in St. Louis, Mis.

Test Kits

Accordingly, a test kit may be prepared for the demonstration of the presence and level of a marker indicative of programmed cell death (such as prostate regression) or cell homeostasis. Generally, such a kit will comprise means for detecting the presence of a marker indicative of prostate regression in a biological sample from a subject, and means for determining whether the marker is present at an increased, or alternatively, decreased level relative to the level present in a corresponding biological sample from a normal subject or from the subject under observation prior to the suspected initiation of programmed cell death, in appropriate containers, and optimally packaged with directions for use of the kit. In one embodiment where prostate regression is being monitored, the cDNA is 10.3, SEQ ID NO:2. In another embodiment such embodiment, the cDNA is 10.30 SEQ ID NO:14. In a preferred embodiment both cDNA 10.3 and 10.30 are used. In yet another embodiment, a marker is a cDNA collection of the present invention enriched for cDNAs that are upregulated during prostate regression. In a specific embodiment of this type the +10 cDNA collection is that having ATCC no. 97807. In still another embodiment a marker is a cDNA collection of the present invention enriched for cDNAs that are downregulated during prostate regression. In a specific embodiment of this type the −8 cDNA collection is that having ATCC no. 97808.

In preferred embodiments, a kit of the invention provides a known amount of the marker to be detected, in which the marker provided in the kit is labeled.

For example, a kit of the invention can provide in an appropriate container or containers:

(a) a predetermined amount of a labeled cDNA collection of the present invention enriched for cDNAs that are upregulated during prostate regression;

(b) if necessary, other reagents; and (c) directions for use of said kit.

More specifically, the diagnostic test kit may comprise:

(a) a known amount of the marker as described above generally bound to a solid phase to form an immunosorbent, or in the alternative, bound to a suitable tag, or plural such end products, etc. (or their binding partners) one of each;

(b) if necessary, other reagents; and (c) directions for use of said test kit.

Another such kit for identifying prostate cells undergoing apoptotic death, may use a single component from a cDNA library of the present invention as a marker, such as a nucleic acid fragment hybridizable to cDNA 10.3, SEQ ID NO:2 the presence of which is indicative of prostate cells undergoing apoptotic death. In preferred embodiments this nucleic acid marker is labeled. In other embodiments two or more such markers may be used as described above.

The present invention may be better understood by reference to the following non-limiting Examples, which are provided as exemplary of the invention.

EXAMPLE

Changing Patterns of Gene Expression Identify Multiple Steps During Regression of Rat Prostate In Vivo

Introduction

It is now apparent that the cellular program mediating cell death is as complex as that regulating cell growth. In view of the complexity of the cell death pathway, and the likelihood that it is not accurately reflected in established tissue culture cell lines, analysis of gene expression during prostate regression in castrated male rats has been chosen as a more appropriate model (Isaacs). In this system, there is a massive programmed death of epithelial and stromal cells in the ventral lobe during the first several days following androgen depletion. That these deaths occur by apoptosis has been extensively documented histologically, and by in situ analysis of DNA fragmentation. Furthermore, some molecules that are differentially regulated during prostate regression have been cloned, and it is clear that their regulation is sensitive to androgen withdrawal and that they can provide early markers for cell death in several tissues.

In the present study, PCR based subtraction hybridization methodology has been employed to prepare cDNA libraries that are highly enriched in clones whose cognate mRNAs are strongly regulated during prostate regression. Characterization of a large number of these cDNA clones demonstrates that at least several hundred genes are strongly regulated during regression and that these include many known genes that have been previously implicated in cell death. Approximately 75% of the identified cDNAs encode previously uncharacterized transcripts or expressed sequence tags (ESTs) have an unknown function. A significant number of these cDNAs identify new members of existing gene families for which functional data is available. Northern blot analysis indicates that the majority of these cDNAs encode mRNAs that are greatly enriched in normal or regressing prostate suggesting a specific role in prostate physiology. However, approximately 5–10% of the encoded mRNAs are also expressed in dying cells during tissue remodeling in response to other stimuli, or in cells undergoing programmed cell death during development, implying a direct role in the cell-death pathway. Comparative in situ hybridization analysis coupled with in situ DNA end labeling studies establishes that there is a temporal progression in the expression of these genes in regressing prostate. Thus, these novels cDNAs provide a rich resource for the initiation of molecular and genetic studies of prostate cell growth and death, and for the identification of new molecules involved in the programmed cell death pathway.

Materials and Methods

Animals and tissue. Male Sprague Dawley rats (250–300 g) were obtained from Charles River Laboratories. Surgical castration by scrotal incision was performed with sodium pentobarbital anesthesia (40 mg/kg). After isolation and ligation of the spermatic cord and arteries, the testis and epididymis were removed. Control animals were anesthetized with surgical incision but were not castrated. Following recovery, ventral prostate glands were dissected from animals 24 to 48 hours after surgery. Tissues were embedded in Tissue Tec O.C.T. medium and frozen directly on dry ice. 15 um tissue sections were cut, mounted onto silicon coated slides, and frozen at −80° C. until needed.

Subtractive Hybridization and Library Preparation. Subtractive hybridization was performed using mRNA isolated from control and regressing rat prostate. For the regressing rat prostate mRNA, samples were polled from mRNA preparations 12, 24 and 48 hours post-castration. These time points were chosen to ensure that very early events during the induction of programmed cell death would be represented in the mRNA populations. Subtractive hybridization was done according to Wang and Brown using eight round of PCR amplification and subtraction for both the −8 and +8 cDNAs. For the +10 cDNA, two additional rounds of subtraction were performed using SGP-2 cDNA as driver. The amplified cDNA preparation were then cloned into λZap (Stratagene) according to protocols supplied by the manufacturer.

In situ hybridization. Tissue sections were fixed in freshly prepared 4% paraformaldehyde in phosphate buffered saline (PBS), pH 7.4 for 10 minutes, washed three times with PBS, and acetylated (0.1 M triethanolamine, 0.25% acetic anhydride, pH 8) for 10 minutes at room temperature. After acetylation, the tissue was permeabilized (0.05% Triton X-100, PBS) for 10 minutes at room temperature, then washed with PBS. Digoxigenin labeled probes were resuspended in 20 mM DT and diluted 1:250–1:500 in preheated hybridization solution (50% formamide, 5×SSC, 5×Denhart's Solution, 250 ug/ml yeast RNA, and 500 ug/ml salmon sperm DNA). Diluted probes were vortexed and heated for 5 min. at 80° C., then immediately chilled on ice for 5 min. Probes were placed onto tissue sections, covered with parafilm and sealed in a humidified chamber. Slides were then incubated overnight at 72° C., incubated in 5×SSC preheated to 72° C. for 5 min., and then in 0.2×SSC for one hour at 72° C. The tissue sections were washed at room temperature in 0.2×SSC and then in buffer B1 (0.1M Tris, 0.1M NaCl, pH 7.5), for 5 min. each. After washes, sections were blocked (1% goat serum/buffer B1) for at least an hour and incubated overnight at 4° C. with a 1:2500 dilution of an alkaline phosphatase (AP) conjugated anti-DIG antibody in buffer B1. After washing three times with B1, the sections were equilibrated in 0.1M Tris, 0.1M NaCl, 50 mM $MgCl_2$, pH 9.5, for 5 min. The sections were also developed in this solution with the addition of 75 mg/ml NBT, 50 mg/ml BCIP, and 0.24 mg/ml levamisol. Development of the reaction was monitored under a microscope and stopped by washing in TE buffer.

Tunel reaction. In situ labeling of nicked DNA was performed according to the instructions in the Boehringer Mannheim cell death detection kit. Tissue sections were fixed for 10–30 min. in 4% paraformaldehyde, then washed in PBS for 30 min. After blocking endogenous peroxidase in the tissue by incubation in blocking solution (0.3% hydrogen peroxide in methanol) for 30 min., the sections were washed in PBS, and then permeabilized (0.1% Triton X-100, 0.1% sodium citrate) for 2 min. at 4° C. Slides were again washed with PBS and incubated with the TUNEL reaction mixture at 37° C. for an hour. After this incubation, slides were washed three times with PBS, and incubated with peroxidase-conjugated anti-fluorescein for 30 min. at 37° C. Slides were washed with PBS, incubated with 3,3 o-Diaminobenzidine (DAB) reaction mixture for 10 min. at room temperature, and washed again in PBS.

Results

Preparation of Libraries Enriched in cDNAs Regulated during Prostate Regression. To decide time points from which to isolate RNA in preparation for the subtractive hybridization analysis, genomic DNA from rat prostate 12, 24, 48 and 72 hours post-castration was isolated and analyzed by Southern blot. In agreement with previously published data, DNA degradation was first observed 24 hours post-castration, peaked at 48 hours and slowly decreased thereafter. Since the changes in gene expression occurring early during prostate regression is most interesting, RNA preparations from the 12, 24 and 48 hour time points were pooled for use in the subtractive hybridization procedure.

An initial attempt to identify cDNAs from genes that are strongly regulated during prostate regression was based on the cDNA display procedure of Liang and Pardee, and on the arbitrarily primed PCR fingerprinting protocol of McClelland and colleagues. The results of these analyses were disappointing, yielding only a small number of abundant regulated transcripts. To improve the recovery of cDNAs representing mRNAs that are either induced or repressed during prostate regression, the PCR based subtractive hybridization procedure of Wang and Brown was employed. Brown and colleagues have used this methodology to isolate cDNAs that are regulated in response to thyroid hormone during amphibian metamorphosis in the tail, limb, and intestine. These studies demonstrated that this procedure can result in identification of large numbers of genes, at least in part because abundant cDNAs that represent the majority of the differential products obtained in the initial enrichment can be removed by further rounds of subtractive hybridization. Furthermore, the enrichment of each cDNA preparation can be monitored by Southern blot analysis of the cDNA populations.

To search for mRNAs that are either induced or repressed during prostate regression, cDNA from normal prostate mRNA, and cDNA from the pooled regressing prostate mRNA, respectively, were used as drivers in the subtraction protocol. To monitor the enrichment of regulated mRNAs during the individual rounds of subtraction hybridization, Southern blots of the resulting amplified cDNAs were probed with a cDNA (−8cDNA) that was isolated as part of the arbitrarily primed cDNA screen mentioned above, with SGP-2 cDNA and with cDNA from the glyceraldehyde phosphate dehydrogenase (GAPDH) gene. As shown in FIG. 1A, the −8cDNA is difficult to detect in the original amplified cDNA preparations and is present only in the minus cDNA. In each round of subtraction, the representation of this cDNA increases in the minus cDNA and decreases in the plus cDNA preparation such that by the eighth cycle of subtraction, this −8cDNA is specifically, highly enriched in the minus cDNA population. In contrast, SGP-2 cDNA is abundant, although differentially expressed in the plus side of the initial amplified cDNA preparations. Its representation is significantly enriched in the plus cDNA preparations in each cycle of subtraction and it is effectively removed from the minus cDNA samples (FIG. 1B). GAPDH cDNA is present in the amplified cDNAs from both control and regressing prostate, and it is effectively removed from both subtractive cDNA preparations as the experiment progresses (FIG. 1C). These results demonstrate that significant enrichment for cDNAs differentially represented in the two initial cDNA populations occurs using this methodology, and that common cDNAs are lost during the successive cycles of subtraction. They also demonstrate that, as observed by Brown and colleagues, both relatively rare and highly abundant cDNAs can be successfully enriched using this protocol.

Figure 2A:
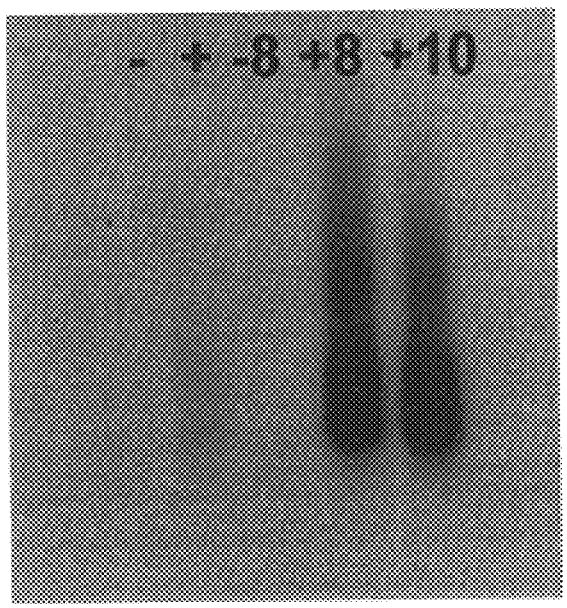
FIG. 2A–B. Removal of SGP-2 cDNA from the +8cDNA by subtractive hybridization yielding the +10 cDNA (ATCC no. 97807) collection. Southern blots showing plus and minus cDNA hybridized with labeled total +10cDNA (FIG. 2A) and SGP-2 cDNA (FIG. 2B).
Figure 2B:
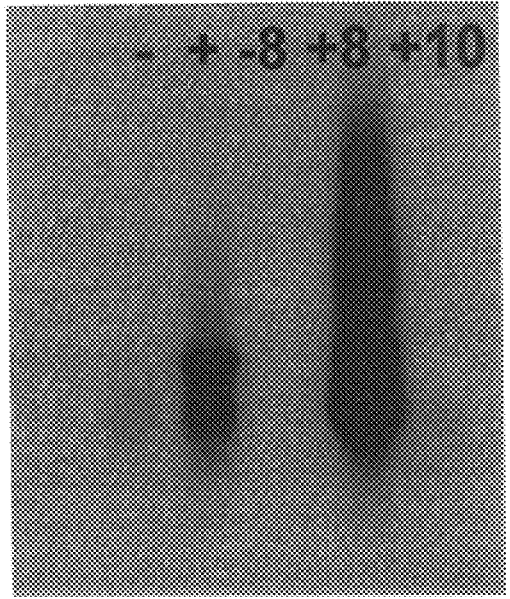
Figure 3A:
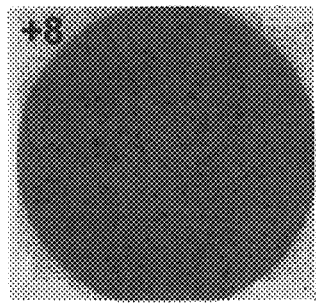
FIG. 3A–D. Individual plates of +8 (FIGS. 3A and 3B) and +10 cDNA libraries (FIGS. 3C and 3D) hybridized to total +10 cDNA (FIGS. 3A and 3C) and SGP-2 cDNA (FIGS. 3B and 3D).
Figure 3B:
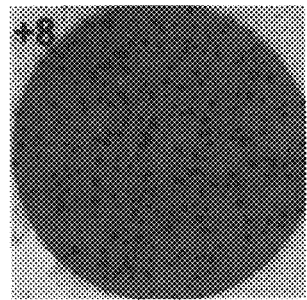
Figure 3C:
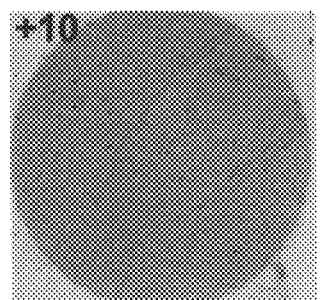
Figure 3D:
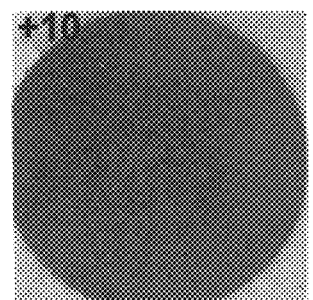
Figure 4A:
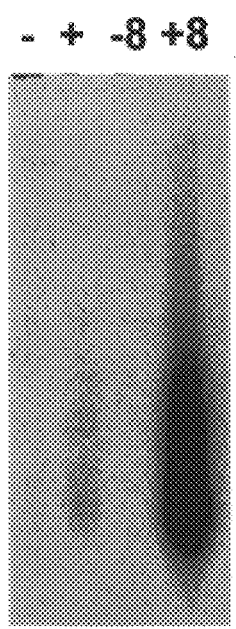
FIG. 4A–D. Abundance and regulation of individual cDNAs as indicated by hybridization of probes 10.19 (FIG. 4A), 10.17 (FIG. 4B), 10.3 (FIG. 4C) and 10.8 (FIG. 4D) to plus and minus cDNA preparations after 0 and 8 rounds of subtractive hybridization.
Figure 4B:
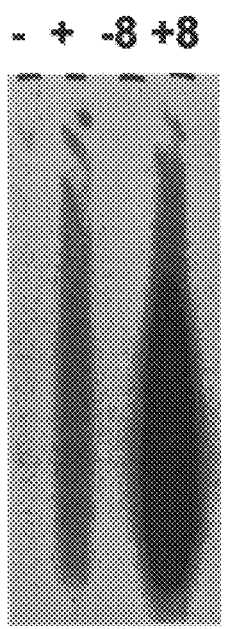
Figure 4C:
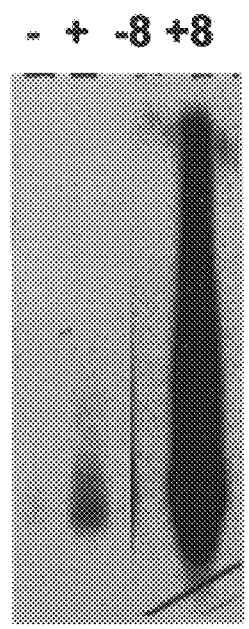
Figure 4D:
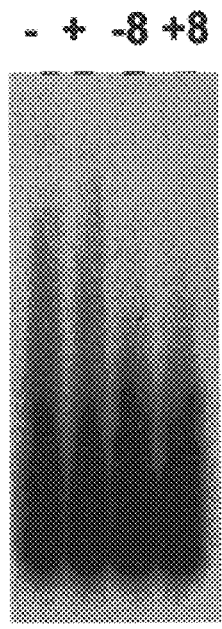

The very strong hybridization of SGP-2 in the plus cDNA preparation suggested that it's strong representation could be problematic in the attempt to identify additional clones that are induced during prostate regression. To overcome this problem, SGP-2 cDNA was employed as driver to subtract the SGP-2 cDNAs from the +8 cDNA preparation. The results of this subtraction are shown in FIGS. 2 and 3. Thus, after two cycles of subtraction with SGP-2 driver, Southern blot analysis indicates that no significant SGP-2 cDNA remains in the +10 cDNA preparation (FIG. 2B). However, using the entire +10 cDNA as a probe yielded signal specifically in the plus cDNA populations (FIG. 2A), indicating that the +10 cDNA retained differential cDNA. To confirm these results, cDNA libraries were prepared from the +8 and +10 cDNA populations in lZAP and screened using both probes. Approximately 40% of the cDNAs detected using the +10 cDNA as probe on the +8 cDNA library were also detected using SGP-2 as probe (compare FIG. 3A and with FIG. 3B). In contrast, none of the clones detected using +10cDNA as probe on the +10 library were detected using SGP-2 as probe (compare FIGS. 3C and FIG. 3D). While these results indicate that SGP-2 cDNA has been completely removed from the +10 cDNA pool and library, they also indicate that some relatively abundant cDNAs may be retained in these preparations since some plaques hybridize significantly more strongly to the complex probe than others (FIG. 3C).

Screening individual clones induced during prostate regression. To begin to assess the complexity of the +10 cDNA library, and to determine whether it contains cDNAs representing novel, strongly regulated mRNAs, thirty individual plaques (10.1–10.30) were isolated, plasmid rescued, and the encoded cDNAs further analyzed (Table 1).

TABLE 1

Characterization of Thirty Individual Isolates.

| CLONE | cDNA BLOT | NORTHERN | TISSUES | SIMIL-ARITY |
|---|---|---|---|---|
| 10.1, 10.4 | Differential | Differential | Prostate + others | GST |
| 10.2, 10.3, 10.6, 10.7 | Differential | Differential | Prostate | novel Lipase |
| 10.5, 10.9 | Differential | Differential | Prostate | novel Cystatin |
| 10.8 | Unregulated | Unregulated | General | Metallopan-stemulin |
| 10.10 | Differential | ND | ND | none |
| 10.11 | Differential | ND | ND | none |
| 10.12 | Differential | Differential | Prostate | Vacuolar ATPase |
| 10.13 | Differential | ND | ND | none |
| 10.15 | Differential | Differential | Prostate | none |
| 10.16, 10.21 | Differential | Differential | Prostate | none |
| 10.17, 10.25 | ND | Differential | Prostate | none |
| 10.18 | Unregulated | Unregulated | General | none |
| 10.19 | Differential | Differential | Prostate | none |
| 10.20, 10.22, 10.24, 10.26 | Differential | Differential | Prostate | none |
| 10.23 | Differential | Differential(?) | General | rp S18 |
| 10.27 | Differential | Differential | General | Thymosin B-4 |
| 10.28 | Differential | Differential | Prostate + others | none |
| 10.29 | Differential | Differential | Prostate | none |
| 10.30 | Differential | Differential | Prostate | none |
| 8.2 | Differential | Differential | Prostate | none |

Cross hybridization analysis of each of these cDNAs to filters containing all thirty individual plaques established that there are twenty two different cDNAs present in this collection. Six clones are represented twice, and one clone is represented four times in these thirty isolates.

As an initial screen to determine whether these twenty-two cDNAs are differentially represented in the subtracted cDNA populations, Southern blots similar to those shown in FIG. 1 were performed for each clone. As indicated in Table 1, nineteen of the twenty-two clones (86%) were enriched during the cycles of subtractive hybridization. It was immediately apparent from this analysis that the representation of specific cDNAs within the subtracted pools varied greatly. To test the utility of this type of prescreen for regulated cDNAs, the intensity of hybridization to the plus and minus cDNA pools with Northern blots from normal and regressing prostate was compared. As shown in FIG. 4, the abundance of the cDNA fragments as represented in the initial and final subtracted cDNA pools generally reflects both the abundance and the degree of regulation of the cognate mRNAs in the tissue as assayed by Northern blot hybridization (see below). Thus, relatively rare mRNAs such as 10.19 are not strongly represented in the initial cDNA preparations, although longer exposures reveal their presence and relative enrichment in the plus cDNA. Abundant mRNAs such as that encoded by the 10.3 cDNA are easily detected even at short exposure times, and the small percentage of cDNAs, that reflect corresponding cognate mRNAs that do not change in abundance during prostate regression, are not differentially represented in the initial cDNA pools. These results indicate that hybridization to the initial amplified cDNA pools can be a very rapid and fairly accurate screen for cDNAs that reflect the presence of corresponding regulated cognate mRNAs.

To determine whether these randomly chosen clones represent previously characterized cDNAs, the nucleotide sequence of each of the twenty-two unique isolates was determined and used to search Genbank with the BlastN and BlastX search programs (NCBI). The results of these searches are shown in Table 1. Of the twenty-two cDNA sequences analyzed, seven (32%) are highly similar to previously characterized cDNAs. Four of these (10.1, 10.8, 10.23 and 10.27) are identical to known genes. Three of these (10.8, 10.23, 10.27) encode abundant, generally expressed genes that are only marginally regulated in regressing prostate. Their presence in the cDNA pool represents the small number of cDNAs that are not significantly differentially regulated in regressing prostate, yet remain present after repeated cycles of subtraction. Clone 10.1 is identical to rat glutathione-S-transferase. This gene has been shown to be strongly regulated during prostate regression in response to castration (Briehl et al., 1991) and during apoptosis of lymphocytes in response to steroids. Its presence, and the presence of the SGP-2 cDNA in the plus 8 subtracted library, confirms that the abundant, regulated mRNAs previously identified in a screen similar to this one are present in the present enriched libraries. Three additional cDNAs have significant homology to previously characterized genes. Clone 10.3 is approximately 70% identical to both human and rabbit gastric lipase. This enzyme is activated during lipid ozonation, triggering the release of endogenous mediators of inflammation. While this enzyme is not known to be regulated during apoptosis, its role in mediating inflammation is consistent with such a role. Since the rat gene for this enzyme has not been reported, we do not yet know whether the cDNA we have identified is simply the rat homologue of the human gene or a related family member. Clone 10.5 is approximately 80% identical to the rat cystatin S gene. The cystatins are a large family of cysteine proteinase inhibitors, some of which are abundant and androgen regulated in normal rat ventral prostate. In this case, two independent isolates of the cDNA were obtained, each having only approximately 80% identity to the previously characterized cystatin S gene. It is probable, therefore, that clone 10.5 encodes a novel member of this gene family. Finally, clone 10.12 encodes a vacuolar ATPase with approximately 55% homology to both the bovine and human vacuolar (H+)-ATPase C subunit mRNAs. The role of this enzyme is to maintain proton and electrochemical gradients across vacuolar membranes. Although. the rat cDNA for this enzyme has not been characterized, we believe the 10.12 cDNA represents a new family member because the human and bovine cDNAs are much more highly homologous to each other than to cDNA 10.12. None of the remaining fifteen cDNAs are strongly similar to any known cDNA.

Figure 5:
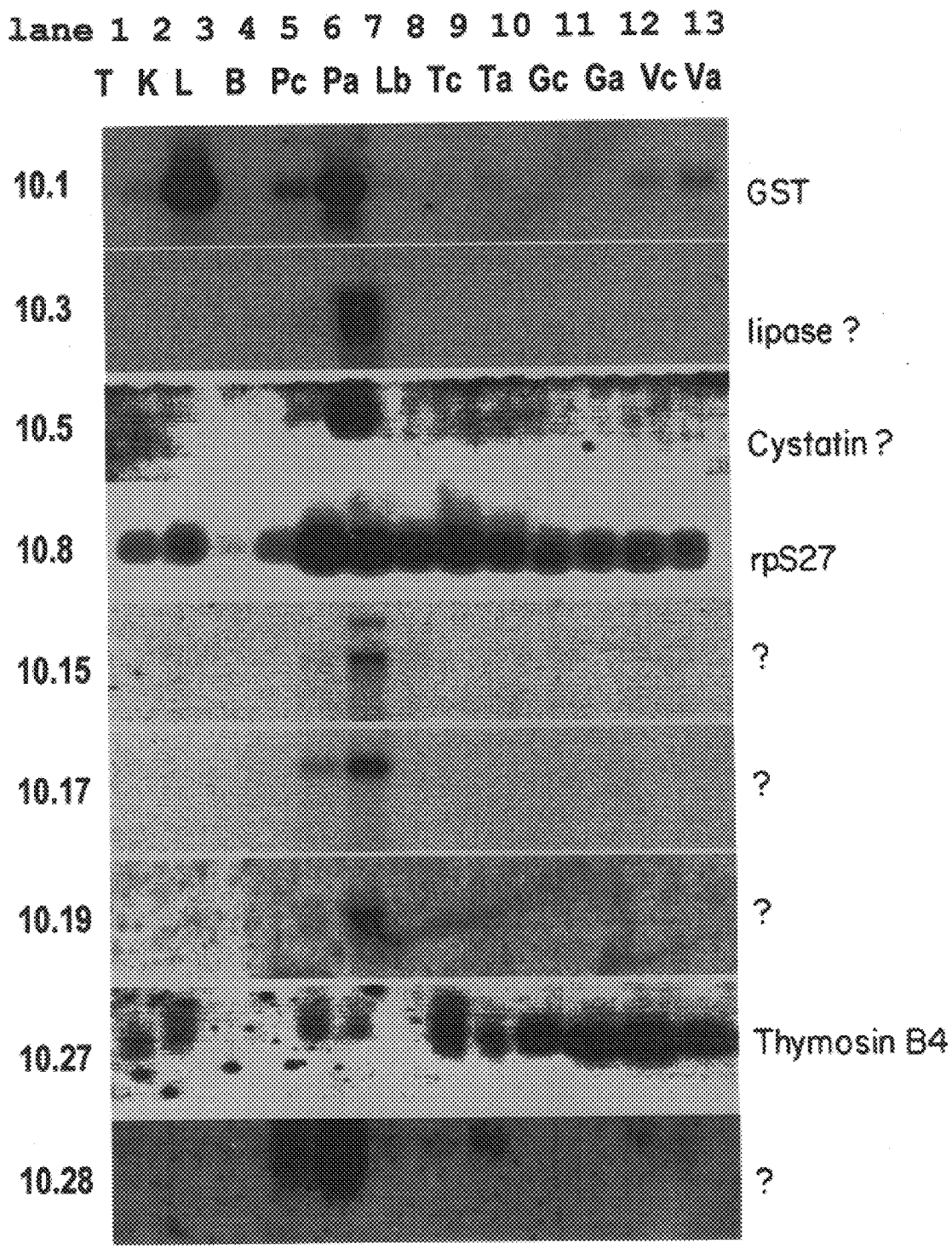
FIG. 5. Northern blots showing regulation of individual cDNAs in regressing prostate and abundance in several other tissues containing significant numbers of dying cells: lane 1 testis; lane 2 kidney; lane 3 liver; lane 4 adult brain; lane 5 control prostate; lane 6 prostate 24 hrs post-castration; lane 7 e12.5–e14.5 limb bud; lane 8 control thymus; lane 9 dexamethasone treated thymus; lane 10 control granulosa cells in culture; lane 11 granulosa cells undergoing apoptosis in culture; lane 12 ventral prostate stromal cells in culture; lane 13 apoptotic ventral prostate stromal cells undergoing apoptosis in culture.

Organ specificity of +10 cDNAs. To assess the magnitude of regulation of individual cDNAs, and determine whether they are expressed predominantly in the prostate or are also expressed in other tissues containing apoptotic cells, Northern blots were performed. Results from ten such blots are shown in FIG. 5. These results confirm those obtained in the prescreen using amplified cDNA to assess regulation (FIG. 4) and those obtained through DNA sequence analysis. Thus, clones that were not strongly regulated in the prescreen or that were homologous to generally expressed mRNAs (10.8, 10.27) appear to be both generally expressed and minimally regulated when analyzed by Northern blot. All other clones, while varying substantially in abundance, are strongly induced in regressing prostate by 24 hours post-castration. Inspection of these Northern blots demonstrates that six of the eight strongly regulated prostate mRNAs are expressed predominantly or exclusively in prostate tissue undergoing regression, while two of the clones appear to be expressed in other tissues containing apoptotic cells. For example, glutathione-S-transferase (GST) mRNA (clone 10.1) is known to be induced in both regressing prostate and thymus from dexamethasone treated mice. The present analysis confirms these results and extends them to include ventral prostate stromal cells undergoing apoptosis in vitro, as well as limb buds isolated from e12.5–e14.5 mouse embryos containing dying interstitial epithelial cells. While GST mRNA expression is correlated with cell death in these situations, its very abundant expression in liver indicates that it is also present in tissues that do not contain significant numbers of apoptotic cells. Clone 10.28, which encodes an mRNA that has not been previously reported, is also expressed in several instances of programmed cell death. Thus, its expression is induced in regressing prostate, in apoptotic primary prostate stromal cells, in dexamethasone treated thymus and in limb bud. It is not present at significant levels in adult brain, liver, kidney or testis. The expression 10.28 mRNA, therefore, closely correlates with cell death in the tissues that we have examined. These results indicate that the vast majority of the cDNAs present in the +10 cDNA library correspond to mRNA transcribed from genes that are both strongly regulated in regressing prostate, and specifically expressed in that tissue. Thus, the cognate genes for the majority of this library are of significant interest for studies of prostate cell physiology. These results also suggest that a relatively small percentage of these genes (10–15%) are of interest for the exploration of the general pathway of programmed cell death.

In situ localization of mRNAs regulated during prostate regression. The system chosen for this analysis is complicated by the fact that the physiologic stimulus causing prostate regression is the severe drop in androgen levels following castration. As a consequence, at least two classes of regulated genes should be present: those that are simply responsive to androgen levels, irrespective of the status of the cell with regard to programmed cell death, and those whose expression is intimately associated with the cell death process itself. These two classes of regulated genes can be identified if assayed in individual cells by in situ hybridization. To gain an appreciation of the number and types of cells in later stages of programmed death in regressing prostate, in situ labeling of nicked DNA was performed at 24 and 48 hours post-castration. As shown in FIG. 6, the gross morphology of ventral prostate is not dramatically altered during the first 48 hours post-castration, although at higher magnifications (FIGS. 6A–6D) one can appreciate that distortion and condensation of epithelial cell nuclei is beginning to occur at 24 hours, and is clearly apparent by 48 hours post-castration. In situ analysis of DNA fragmentation indicates that only a very small percentage of cells in the ventral prostate are in late stages of cell death by 24 hours post-castration, whereas this number significantly increases at least ten fold by 48 hours. These observations are in close agreement with those of Zirkin and colleagues, although in the present experiments the number of stromal cells revealed by in situ DNA fragmentation assays at both time points is very small.

It seems likely given these results that genes whose regulation is directly responsive to circulating androgen levels will be induced or repressed in most prostate epithelial cells coincidently, whereas those regulated as a consequence of programmed cell death will be regulated at the single cell level with the regulation being observed in increasing numbers of cells between 24 and 48 hours post-castration. As shown in FIG. 7, the present in situ hybridization analysis is consistent with this supposition. Clones 15.85, PBK4 and PBK14 are each strongly down regulated after castration when analyzed by Northern hybridization. In these cases, in situ hybridization indicates that the MRNA is specific for prostate epithelial cells, and that they disappear from the entire epithelial cell population in synchrony. While the disappearance of 15.85 mRNA clearly precedes that of PBK4 and PBK14, the fact that all of the cells lining the ducts behave similarly with respect to these changes in gene expression demonstrates that there is a rapid and synchronous response of this cell population to changing hormone levels. This is further supported by the appearance of 10.17 mRNA in all prostate epithelial cells at 48 hours post-castration. These results clearly document that the entire population of epithelial cells in ventral prostate responds to castration by altering gene expression patterns both positively and negatively. Most likely these genes represent direct targets for regulation by the androgen receptor.

Our analysis of clones isolated from the +10 cDNA library, however, indicates that the majority do not appear in synchrony in prostate epithelial cells following castration. Rather, their regulation evidently occurs independently in single cells as regression proceeds. The results for three such mRNAs (10.1, 10.3, 10.28) are shown in FIG. 8. Clone 10.1, which encodes rat glutathione-S-transferase, is not detectable in control prostate tissue by in situ hybridization. At twenty four hours post-castration, individual strongly positive cells are evident, with the number of positive cells significantly increasing between 24 and 48 hours post-castration. Similar results are obtained with clone 10.28, which encodes a novel mRNA that is also expressed in other tissues containing apoptotic cells (FIG. 5). Given the expression of GST and 10.28 in several tissues containing apoptotic cells, it is not surprising that their expression does not correlate with hormonal status per se, but that they appear to be regulated in individual cells in a pattern consistent with programmed cell death. This pattern of expression is also seen with clone 10.3, which encodes a protein with very high homology to pregastic lipase. In this case, however, Northern blot analysis revealed a very strongly regulated mRNA that is not expressed at detectable levels in other tissues (FIG. 5). Thus, our in situ hybridization studies suggest at least three classes of gene regulation during prostate regression: 1) genes such as 15.85, pBK4, pBK14 and 10.17 are regulated in all prostate epithelial cells, presumably as a direct consequence of falling androgen levels after castration; 2) genes such as 10.1 and 10.28 that are regulated in individual cells in regressing prostate whose expression in other tissues suggests general responsiveness to apoptotic death; 3) and genes such as 10.3 that are regulated in prostate epithelial cells undergoing apoptotic death but can not be detected in other apoptotic cells. While our results can not be construed as evidence that the latter two categories of regulated genes are functionally important in the cell death effector pathway, they are certainly strong candidates for such a role. Alternatively, these genes may simply be responsive to physiological changes occurring in these cells as they initiate cell death and, as such, they may represent markers rather than direct participants in apoptosis. Functional analysis of their encoded products will be required to distinguish between these possibilities.

Discussion

Genetic characterization of programmed cell death during C. elegans and D. melanogaster development have provided a framework for further investigation of cell death and its regulation. Consideration of these studies in the light of more recent studies of molecular mechanisms of cell death in vertebrates have revealed a complex program that involves an array of both regulatory and effector genes. Several clear conclusions can be drawn from this work that are relevant to the present study. First, a wide array of proteins can induce or suppress cell death if ectopically activated in a particular cell type. Second, programmed cell death in a given cell type may be regulated by pathways that are specific to that cell type. Third, several classes of molecules appear to be fundamental to the effector mechanisms for cell death in a wide variety of circumstances. Fourth, extracellular ligands can have a crucial initiating role in selecting cells for an apoptotic fate. Finally, it is not yet possible to delineate rate limiting steps for the cell death pathway in many well characterized paradigms for programmed cell death in vertebrates.

The purpose of the present study was to gain insight into the complexity of the cell death program that is activated during prostate regression in response to castration, and to identify novel molecules that are either implicated in prostate regression specifically or expressed more generally in multiple cases of programmed cell death in vivo. The approach taken is to clone a large number of cDNAs whose cognate mRNAs are very strongly regulated in prostate epithelial cells following castration, and to screen among them for molecules that are either appear to be specifically induced in dying prostate epithelial cells or that are more generally expressed in tissues containing significant numbers of apoptotic cells. The detailed analysis of the plus cDNA library has demonstrated that it is highly enriched in cDNAs representing mRNAs that are strongly induced during prostate regression: 85–90% of the clones are regulated when assayed by Northern blot or in situ hybridization. Cross hybridization studies and DNA sequence analysis indicates that the number of genes that are induced during prostate regression is large. Thus, twenty two different genes are represented in the thirty clones sequenced in this study. Of these genes, seven (approximately 30%) are either known genes or very closely related to genes with known functions. The remaining cDNAs (approximately 70%) either have not been previously cloned (approximately 50%), or are homologous to expressed sequence tags (approximately 20%) of unknown function. These values have been confirmed by extensive DNA sequence analysis demonstrating the presence of at least several hundred different cDNAs in the plus cDNA library that are distributed similarly between known and unknown genes.

The identity of the known genes found in this screen supports the conclusion that many of these genes could have a direct role in death of prostatic epithelial cells. Thus, SGP-2, GST, and thymosin B4 have all been implicated in apoptosis. While no direct evidence has been reported to implicate cystatin C, pregastric lipase or vacuolar ATPase in cell death, a role for these molecules in tissue regression can be envisaged. The only genes identified in this screen that do not have an obvious function regarding prostate regression are the two ribosomal genes represented in this collection of cDNAs (Table 1). However, since these cDNAs appear to be only marginally regulated during prostate regression and are otherwise generally expressed, they could represent a small background of false-positive cDNAs that could, in theory, contaminate this library. On the other hand, it is at least as likely that even the cognate RNAs corresponding to these cDNAs play a role in prostate regression which has not yet been elucidated. In either case, it has been demonstrated that this library is highly enriched in cDNAs representing genes that are strong candidates for a direct role in prostate physiology, and that a small percentage of these genes may have a direct role in a fundamental cell death program.

In situ hybridization studies reveal several features of prostate regression that have not been explicitly demonstrated in prior studies. For example, it is now clear that there is a rapid and synchronous response of all epithelial cells in the rat ventral prostate following castration. Several genes are repressed (15.85, pBK4, pBK14) and at least one gene is induced (10.17) in nearly all prostatic epithelial cells within the first two days of castration. Since the in situ assays for DNA fragmentation suggest that very few cells are in late stages of cell death at 24 hours, it is probable that all of the epithelial cells undergo a dramatic change in phenotype in response to androgen withdrawal. This is consistent with the decrease in wet weight that is initiated within the first 48 hours following castration in all lobes of the prostate, in spite of the fact that significant cell death is observed only in the ventral lobe. These genes may be direct targets of androgen action rather than participants in, or markers of, programmed cell death.

In addition, the strong induction of several genes (e.g. 10.1, 10.3, 10.28) in a significant number of individual epithelial cells in ventral prostate at 24 hours post-castration, prior to significant labeling of cells using the DNA fragmentation assay and concurrent with the changes of gene expression occurring in all prostatic epithelial cells in response to hormones, suggests that the initial stages of cell death in this tissue are marked by changes in gene expression that occur in single cells. This is consistent with the asynchronous appearance of late stage apoptotic cells as revealed in the DNA fragmentation assays, supporting the view that it is the asynchronous initiation of cell death in individuals cells rather than a varying temporal progression in the death program that is responsible for the disappearance of cells from ventral prostate over time. Furthermore, the differences in the number of cells expressing these markers at 24 and 48 hours post-castration versus the number of cells containing fragmented DNA strongly suggests that many hours must pass between the initiation of the death pathway in individual cells and their eventual demise by DNA fragmentation. Thus there appears to be a temporal progression in the expression of these genes in regressing prostate. Finally, comparison of the in situ hybridization and Northern blot results clearly indicates that both prostate specific (e.g. 10.3) and general (10.1, 10.28) markers of cell death are present within this library. Functional analysis of these genes to discover molecular mechanisms underlying both the tissue specific and general features of apoptotic death in this system will prove to be valuable in the study of prostate regression and programmed cell death in general.

The identification of a large number of novel cDNAs from regressing prostate provide an important avenue toward deepening our understanding of the physiology of prostate growth and death. Some of these genes provide excellent markers for the events underlying abnormalities in prostate growth. Others encode critical regulatory molecules that could play direct roles in benign prostate hyperplasia or prostate cancer. In addition, it is probable that among these genes are as yet unrecognized regulators of programmed cell death that may play critical roles in other tissues.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated nucleic acid comprising the nucleotide sequence selected from the group consisting of SEQ ID NO:2, SEQ ID NO:5, SEQ ID NO:6, SEQ ID NO:7, SEQ ID NO:8, SEQ ID NO:9, SEQ ID NO:12, SEQ ID NO:13, and SEQ ID NO:14.

2. A nucleic acid consisting of the isolated nucleic acid of claim 1 and a heterologous nucleotide sequence.

3. A labeled oligonucleotide probe that hybridizes with the nucleic acid of claim 1 under standard hybridization conditions.

4. The isolated nucleic acid of claim 1 wherein the nucleic acid comprises the nucleotide sequence of SEQ ID NO:2.

5. The isolated nucleic acid of claim 1 wherein the nucleic acid comprises the nucleotide sequence of SEQ ID NO:5.

6. The isolated nucleic acid of claim 1 wherein the nucleic acid comprises the nucleotide sequence of SEQ ID NO:6.

7. The isolated nucleic acid of claim 1 wherein the nucleic acid comprises the nucleotide sequence of SEQ ID NO:7.

8. The isolated nucleic acid of claim 1 wherein the nucleic acid comprises the nucleotide sequence of SEQ ID NO:8.

9. The isolated nucleic acid of claim 1 wherein the nucleic acid comprises the nucleotide sequence of SEQ ID NO:9.

10. The isolated nucleic acid of claim 1 wherein the nucleic acid comprises the nucleotide sequence of SEQ ID NO:12.

11. The isolated nucleic acid of claim 1 wherein the nucleic acid comprises the nucleotide sequence of SEQ ID NO:13.

12. The isolated nucleic acid of claim 1 wherein the nucleic acid comprises the nucleotide sequence of SEQ ID NO:14.

13. A nucleic acid consisting of the isolated nucleic acid of claim 4 and a heterologous nucleotide sequence.

14. A labeled oligonucleotide probe that hybridizes with the nucleic acid of claim 4 under standard hybridization conditions.

15. A nucleic acid consisting of the isolated nucleic acid of claim 5 and a heterologous nucleotide sequence.

16. A labeled oligonucleotide probe that hybridizes with the nucleic acid of claim 5 under standard hybridization conditions.

17. A nucleic acid consisting of the isolated nucleic acid of claim 6 and a heterologous nucleotide sequence.

18. A labeled oligonucleotide probe that hybridizes with the nucleic acid of claim 6 under standard hybridization conditions.

19. A nucleic acid consisting of the isolated nucleic acid of claim 7 and a heterologous nucleotide sequence.

20. A labeled oligonucleotide probe that hybridizes with the nucleic acid of claim 7 under standard hybridization conditions.

21. A nucleic acid consisting of the isolated nucleic acid of claim 8 and a heterologous nucleotide sequence.

22. A labeled oligonucleotide probe that hybridizes with the nucleic acid of claim 8 under standard hybridization conditions.

23. A nucleic acid consisting of the isolated nucleic acid of claim 9 and a heterologous nucleotide sequence.

24. A labeled oligonucleotide probe that hybridizes with the nucleic acid of claim 9 under standard hybridization conditions.

25. A nucleic acid consisting of the isolated nucleic acid of claim 10 and a heterologous nucleotide sequence.

26. A labeled oligonucleotide probe that hybridizes with the nucleic acid of claim 10 under standard hybridization conditions.

27. A nucleic acid consisting of the isolated nucleic acid of claim 11 and a heterologous nucleotide sequence.

28. A labeled oligonucleotide probe that hybridizes with the nucleic acid of claim 11 under standard hybridization conditions.

29. A nucleic acid consisting of the isolated nucleic acid of claim 12 and a heterologous nucleotide sequence.

30. A labeled oligonucleotide probe that hybridizes with the nucleic acid of claim 12 under standard hybridization conditions.

31. An isolated nucleic acid comprising the nucleotide sequence SEQ ID NO:15.

32. A nucleic acid consisting of the isolated nucleic acid of claim 31 and a heterologous nucleotide sequence.

33. A labeled oligonucleotide probe that hybridizes with the nucleic acid of claim 31 under standard hybridization conditions.

34. A method of identifying a mammalian prostate cell suspected of undergoing apoptosis comprising:

(a) contacting sample mRNAs with an oligonucleotide probe under high stringency hybridization conditions; wherein said sample mRNAs are collected from said mammalian prostate cell suspected of undergoing apoptosis; and wherein the oligonucleotide probe is derived from a nucleotide sequence selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:12, SEQ ID NO:13, and SEQ ID NO:14;

(b) determining the amount of hybridization between said sample mRNAs and the oligonucleotide probe; and (c) comparing the determined amount of hybridization in step (b) with the amount of hybridization between the oligonucleotide probe and control mRNAs from a normal mammalian prostate cell; wherein an increase in the amount of hybridization with said sample mRNAs as compared to the control mRNAs is indicative of said prostate cell undergoing apoptosis.

35. A method of identifying a mammalian prostate cell suspected of undergoing apoptosis comprising:

(a) contacting sample mRNAs with an oligonucleotide probe under high stringency hybridization conditions; wherein said sample mRNAs are collected from said mammalian prostate cell suspected of undergoing apoptosis; and wherein the oligonucleotide probe is derived from the nucleotide sequence of SEQ ID NO:15;

(b) determining the amount of hybridization between the sample mRNAs and the oligonucleotide probe; and (c) comparing the determined amount of hybridization in step (b) with the amount of hybridization between the oligonucleotide probe and control mRNAs from a normal mammalian prostate cell; wherein a decrease in the amount of hybridization of the sample mRNAs as compared to the control mRNAs is indicative of said mammalian prostate cell undergoing apoptosis.

36. A method of identifying a protein that is encoded by a cDNA in an upregulated mammalian prostate cDNA collection comprising:

(a) contacting mRNAs with an oligonucleotide probe under high stringency hybridization conditions; wherein the mRNAs are collected from a mammalian prostate cell; and wherein the oligonucleotide probe is derived from a particular cDNA contained in the an upregulated mammalian prostate cDNA collection; wherein said cDNA collection comprises a cDNA having a nucleotide sequence selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:12, SEQ ID NO:13, and SEQ ID NO:14;

(b) detecting an mRNA that hybridizes with the oligonucleotide probe; and (c) identifying the protein encoded by the mRNA; wherein the protein is identified as being encoded by a cDNA in the upregulated mammalian prostate cDNA collection.

37. The method of claim 36 wherein the upregulated mammalian prostate cDNA collection is the cDNA collection having the ATCC no. 97807.

38. The method of claim 36 wherein said contacting is performed in an array of multiple sampling chambers.

39. A method of identifying a protein that is encoded by a cDNA in a downregulated mammalian prostate cDNA collection comprising:

(a) contacting mRNAs with an oligonucleotide probe under high stringency hybridization conditions; wherein the mRNAs are collected from a mammalian prostate cell; and wherein the oligonucleotide probe is derived from a particular cDNA contained in a downregulated mammalian prostate cDNA collection; wherein said cDNA collection comprises a cDNA having a nucleotide sequence of SEQ ID NO:15;

(b) detecting an mRNA that hybridizes with the cDNA; and (c) identifying the protein encoded by the mRNA; wherein the protein is identified as being encoded by a cDNA in the downregulated mammalian prostate cDNA collection.

40. The method of claim 39 wherein the downregulated cDNA collection is the cDNA collection having the ATCC no. 97808.

41. The method of claim 39 wherein said contacting is performed in an array of multiple sampling chambers.

* * * * *